United States Patent [19]
Karn et al.

[11] Patent Number: 6,114,109
[45] Date of Patent: *Sep. 5, 2000

[54] VIRAL (HIV) GROWTH INHIBITION

[75] Inventors: Jonathan Karn, Little Shelford; Michael J. Gait, Cambridge; Shaun Heaphy, Leicester; Colin Dingwall, Cambridge, all of United Kingdom

[73] Assignee: RiboTargets, Ltd., Cambridge, United Kingdom

[*] Notice: This patent is subject to a terminal disclaimer.

[21] Appl. No.: 09/083,756

[22] Filed: May 22, 1998

Related U.S. Application Data

[62] Division of application No. 08/541,950, Oct. 10, 1995, Pat. No. 5,821,046, which is a continuation of application No. 07/960,370, Mar. 19, 1993, abandoned, and a division of application No. PCT/GB91/01321, Aug. 2, 1991.

[30] Foreign Application Priority Data

Aug. 2, 1990 [GB] United Kingdom .................... 9016973

[51] Int. Cl.⁷ ..................................................... C12Q 1/00
[52] U.S. Cl. ................... 435/4; 435/6; 536/23.1
[58] Field of Search ................... 536/23.1; 435/4, 435/6

[56] References Cited

U.S. PATENT DOCUMENTS 5,821,046  10/1998  Karn et al. .................................. 435/4

OTHER PUBLICATIONS

Dingwall et al., Proc. Natl. Acad. Sci. USA 86:6925–6929 (1989).

*Primary Examiner*—Remy Yucel
*Attorney, Agent, or Firm*—Kathleen M. Williams

[57] ABSTRACT

A synthetic molecule comprises at least one oligonucleotide, comprising and RNA binding sequence or sequences corresponding to the site bound by the HIV protein tat and capable of binding to tat within cells. The binding sequence or sequences, by binding tat within cells, can act to cause inhibition of growth of any HIV present in the cells, and so has potential therapeutic use in treatment of patients affected with HIV. The invention also provides an assay for identifying compounds that inhibit tat binding.

3 Claims, 21 Drawing Sheets

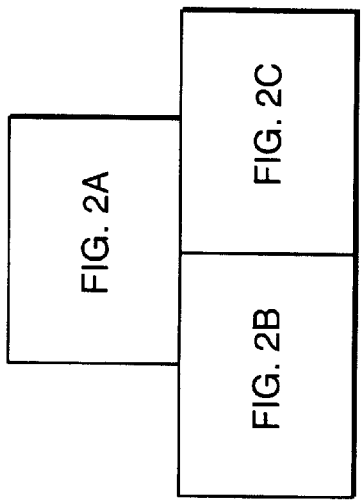
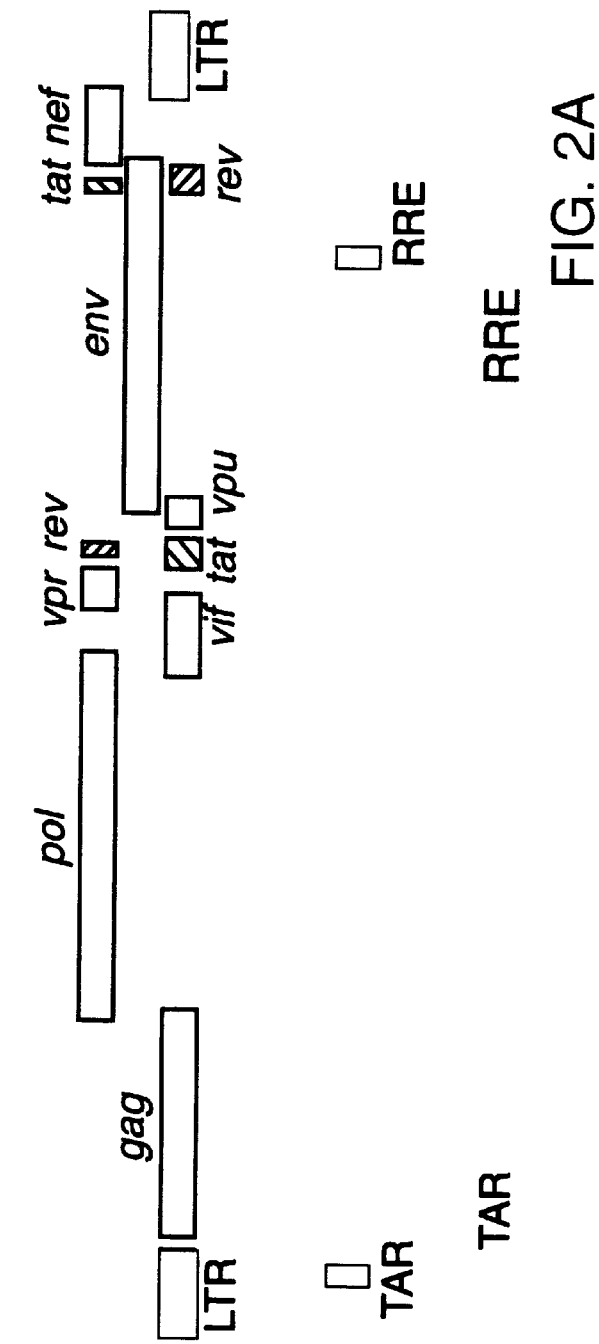

U→G (bulge)

ΔU (bulge)

G→U (loop)

```
                              A                 C U
                      U U GAGC    G
         C          A       CCAGA U  AGC
     GGU  UCUCUGGUUAG         |||| CUG
 GGG                          GGUCU    AG
 |||                          CUCG
 CCC  AGGGAUCAAUC         40
         50

FIG. 18a
```

```
         U U U GAGC C U G
G—CCAGA         AGC
        GGUCU   CUG
C—GGUCU         AG
         CUCG

FIG. 18b
```

```
            U U U GAGC—AGC
AG—CCAGA
            GGUCU   CUG
UC—GGUCU    CUCG—UCG

FIG. 18c
```

VIRAL (HIV) GROWTH INHIBITION

This is a divisional application of prior U.S. application Ser. No. 08/541,950, filed Oct. 10, 1995, now U.S. Pat. No. 5,821,046, which is a continuation of U.S. application Ser. No. 07/960,370, filed Mar. 19, 1993, now abandoned, which is a national stage application of PCT/GB91/01321, filed Aug. 2, 1991.

FIELD OF THE INVENTION

This invention relates to a method of and compositions for use in the inhibition of viral growth within cells. Specifically, the invention relates to the inhibition of growth of the human immunodeficiency virus (HIV).

BACKGROUND TO THE INVENTION

Transcription of the HIV genome during virus replication shows distinct kinetic phases (see references 53, 59, 60, 79). The initial products of HIV gene expression are short, multiply spliced mRNAs approximately 1.8 to 2.0 kb in length, which encode the trans-acting regulatory proteins tat, rev (and possibly nef). As infection by the virus develops, and the levels of the tat and rev proteins rise in the infected cells, mRNA production shifts progressively towards production of a family of singly-spliced 4.3 kb mRNAs encoding env and other HIV gene products such as vif and vpr. Finally, late in the infection process, production switches to fill-length, unspliced, transcripts which act both as the virion RNA and the mRNA for the gag-pol polyprotein.

To achieve this control of gene expression, the HIV virus relies on the interaction of cellular and virus-encoded trans-acting factors with cis-acting viral regulatory sequences (1, 3, 53). Initiation of transcription relies largely on the presence of binding sites for cellular transcription factors in the viral long terminal repeat (LTR) (28). In contrast, the virally encoded regulatory proteins tat and rev exert their activity via cis-acting sequences encoded within HIV messenger RNAs. The transactivation-responsive region (TAR) is required for tat activity, and is located in the viral long terminal repeat (LTR) between residues +1 and +79 (5, 9, 10, 11, 12, 13, 14, 16, 27, 38). The rev-responsive element (RRE) has been localized to a 243-nucleotide long sequence within the env gene (47, 51, 54, 65, 67, 68, 77). Similar regulatory proteins and target sequences are used by HIV-2 and SIV (8, 66). The HTLV-1 virus rex gene product appears to function analogously to rev, and can functionally substitute for rev to promote viral gene expression (76).

The distinct kinetic phases of HIV transcription are now believed to reflect the intracellular levels of the regulatory proteins tat and rev. Initially, binding of host transcription factors to the LTR induces basal level transcription of the early mRNAs including tat. As tat levels rise, increased transcription from the LTR is stimulated by the trans-activation mechanism. This leads to further increases in tat levels, and also stimulates production of rev. Production of the viral structural proteins begins once rev levels have risen to sufficiently high levels to promote export of messenger RNAs carrying the rev-responsive element (RRE) sequence. The HIV growth cycle may also include a latent stage where viral gene expression is silent because transcription from the viral LTR produces insufficient amounts of regulatory proteins to initiate the lytic growth cycle. Significant levels of HIV gene expression are only achieved in the presence of tat protein. Initially, it seemed most likely that tat activity produced an increased rate of transcription initiation either by stimulating binding of host transcription factors to sequences in viral LTR or by acting as a transcription factor itself (1, 3, 53). However, several experiments strongly suggest that tat activity requires RNA target sequences rather than DNA target sequences.

Deletion analysis of the viral LTR showed that tat activity requires a regulatory element located downstream of the initiation site for transcription, at the 5-terminus of all the mRNA transcripts between residues +1 and +79, called the trans-activation-response region (TAR) (5, 10, 11, 27, 28). The placement of TAR in a transcribed region was surprising, since this suggested that it could function as an RNA rather than as a DNA element. Support for this idea came from observation that unlike enhancer elements, the TAR element is only functional when it is placed 3' to the HIV promoter, and in the correct orientation and position (5, 12–15). Furthermore, the TAR RNA sequence forms a highly stable, nuclease-resistant, stem-loop structure, and point mutations which destabilize the TAR stem by disrupting base-pairing usually abolish tat-stimulated transcription (88).

Berkhout et al. (16) provided convincing evidence that the TAR RNA sequence must be transcribed in the nucleus and correctly folded in order for trans-activation to occur. They introduced antisense sequences, designed to destabilize formation of TAR RNA hairpin-loop structures either upstream or downstream of TAR. Both the correct folding of TAR and trans-activation were blocked when the destabilizing sequences were placed on the 5'-side of TAR, but placement of the same sequences on the 3'-side of TAR allowed normal trans-activation. This strongly suggested that the TAR hairpin-loop structure could fold and become active on nascent transcripts.

Trans-activation does not appear to be due to tat regulation of DNA-binding proteins to upstream promoter elements (17) since viral LTRs truncated upstream of the Spl sites (18) or fused to heterologous promoters (5, 19, 20) may be trans-activated.

In tat-expressing cells both mRNA levels, as measured by hybridization, and nuclear transcription rates, as measured by run-on experiments, are increased 7 to 40 fold (88, 89). Although there has been considerable debate about whether tat could also increase the translation efficiency of mRNAs carrying TAR, it now seems clear that the increase in mRNA synthesis promoted by tat is sufficient to account for trans-activation. Accurate measurements of both CAT mRNA and CAT protein levels in transfected cells, show that protein accumulated in parallel to the mRNA over a broad range. At very low levels of CAT mRNA translation is less efficient than at high levels of message. However this increase in RNA utilization is not tat-specific since any increase in mRNA levels, such as after stimulation of transcription by adenovirus EIA protein, produces a corresponding effect on translation (89).

One case where translational control of TAR-containing mRNAs by tat has been reported to be active is in Xenopus oocytes. When CAT mRNAs carrying TAR sequences are injected into the cytoplasm of Xenopus oocytes they are not translated, but translation is restored after co-injection of the mRNA into the nucleus together with tat protein (90). This phenomenon could be a reflection of a specialized mechanism in Xenopus; translational control by tat could not be demonstrated when parallel microinjection experiments were performed in mammalian cells permissive for HIV growth (91). It is also possible that the translation block observed in the Xenopus experiments is due to contamination of the mRNA preparations by double-stranded RNA fragments produced during in vitro transcription by bacterial RNA polymerases. In mammalian cell free translation systems TAR-containing mRNAs were reported to be translated poorly because the TAR sequence appeared to activate the double-stranded RNA-dependent kinase (92). However, after re-purification of preparations of the TAR-containing-RNAs by chromatography on cellulose columns, contaminating double-stranded RNAs were removed and the TAR-containing mRNA preparations were translated normally (93).

Although the simplest explanation for the ability of tat to stimulate transcription from promoters that carry the TAR sequence is that tat recognizes TAR RNA by direct binding, demonstration of this interaction proved to be difficult. Early attempts to demonstrate specific binding of tat to TAR RNA were probably unsuccessful because it is difficult to purify tat expressed in *E. coli* free from RNA contaminants and under conditions where aggregates are not formed due to oxidation of its seven cysteine residues. However, using an improved method we were able to demonstrate that tat is able to specifically recognize TAR RNA. Binding shows high affinity ($K_d$=12 nM) and tat forms one-to-one complexes with TAR RNA (94).

Tat recognition of TAR requires only the presence of a U-rich bulge near the apex of the TAR RNA stem as well as closely flanking base-pairs. Mutations which alter the U-rich bulge sequence, or which affect the structure of the U-rich bulge by disrupting base-pairing in nearby residues of the TAR stem-loop structure, abolish both tat binding and trans-activation (10, 11, 27, 28). By contrast, the identity of many of the base pairs throughout the TAR stem does not appear to be an important requirement for transactivation or for tat binding so long as Watson-Crick base pairing is maintained. RNA binding by tat almost certainly involves the formation of specific salt bridges between arginine residues on tat and phosphates on the TAR RNA. C-terminal peptides carrying an arginine-rich sequence from tat are also able to bind to TAR RNA at the U-rich bulge, although the peptides bind with less specificity and lower affinity than the intact protein (95, 96).

Experiments using hybrid proteins containing tat and an exogenous RNA-binding domain have provided interesting genetical evidence supporting the biochemical evidence that tat is presented to the transcription machinery after binding directly to nascent transcripts carrying the TAR RNA element (97, 98). For example, fusion proteins containing sequences from tat and bacteriophage R17 coat protein can stimulate transcription from HIV LTRs when the TAR RNA sequence is replaced entirely by a RNA stem-loop structure carrying the RI 7 operator sequence. As in the case of tat recognition of TAR RNA, binding appears to be direct, since mutations in the RI 7 RNA operator sequence that reduce its affinity for coat protein produce a corresponding decrease in trans-activation by the tat RI 7 fusion protein in vivo (98).

How does tat regulate gene expression after binding to TAR RNA? One early suggestion was that TAR acts to stimulate transcription initiation rates, by acting as an additional loading site for transcription factors (99). Although difficult to rule out, this model seems increasingly unlikely since hybrid promoters including promoters that contain only binding sites for fusion proteins containing the yeast GAL-4 binding domain are highly responsive to tat. It should also be noted that there are no known examples of RNA binding proteins that affect transcriptional initiation whereas there are many good examples in prokaryotic systems of RNA binding proteins, such as the bateriophage lambda N protein, that control transcriptional elongation.

Peterlin and his colleagues made the important suggestion that tat acts as an anti-terminator which helps to overcome a block to elongation at or near the TAR site (38, 40, 98). Their proposal is based on observations that short, prematurely-terminated RNA transcripts accumulate in the absence of tat. However TAR is not simply a site of anti-termination since mutations in TAR which abolish trans-activation, or deletions of TAR, do not result in constitutively high levels of LTR expression and it is difficult to "chase" the short RNA transcripts into full-length mRNAs. The failure to identify a specific terminator sequence downstream of TAR has led to a third proposal in which tat acts as a more general elongation factor for RNA polymerase II and not simply as a site-specific anti-termination factor. It seems likely that tat and cellular co-factors assemble with the RNA polymerase II soon after transcriptional initiation in a reaction mediated by the protein binding sites present on the TAR-containing nascent transcripts. This modified transcription complex then stimulates viral mRNA production by overcoming additional blocks to elongation at a variety of distal sites, including TAR.

Strong support for the elongation factor model comes from nuclear run-on experiments. In the absence of tat RNA polymerases can only be found at or near the viral LTR. However, the density of RNA polymerases downstream of the promoter increases dramatically in the presence of tat (89). However, a rigorous demonstration of an elongation-dependent mechanism will require the development of efficient cell free transcription systems that respond to tat. There are encouraging signs that these will soon be available. Addition of extracts from HIV-infected cells stimulates transcription from the viral LTRs (100). There has also been a recent report that bacterially synthesized tat can stimulate transcription in vitro. Unfortunately, stimulation of transcription by the recombinant tat is best observed only after extended incubations with high concentrations of added protein (101). It therefore remains unclear whether genuine trans-activation has been reproduced in vitro, and additional development of the cell free systems will be required before mechanistic studies can begin.

It is an aim of the present invention to provide an effective method for, and compositions for use in, the inhibition of HIV viral growth within cells, which involves modifying the activity of the regulatory protein tat in the viral growth cycle, and also an assay for screening potential anti-viral agents.

STATEMENT OF THE INVENTION

According to a first aspect of the present invention there is provided a synthetic molecule comprising at least one oligonucleotide comprising an RNA binding sequence or sequences corresponding to the site bound by the HIV protein tat and capable of binding to tat within cells.

The binding sequence or sequences, by binding tat within cells, can act to cause inhibition of the growth of any HIV present in the cells, and so has potential therapeutic use in treatment of patients infected with HIV.

According to a second aspect of the present invention, there is provided a pharmaceutical composition comprising a molecule as provided by the first aspect of the invention. The pharmaceutical composition is conveniently for use as an inhibitor of growth of HIV within cells.

According to a third aspect of the invention, there is provided a synthetic molecule for use in treating patients infected with HIV, the molecule comprising at least one oligonucleotide comprising an RNA binding sequence or sequences corresponding to the site bound by the HIV protein tat and capable of binding to tat within cells.

According to a fourth aspect of the invention, there is provided the use of a molecule as provided by the first aspect of the invention, in the manufacture of a medicament for inhibiting growth of HIV within cells.

The present invention is based around the unexpected discovery that only a very small and specific region of the TAR sequence is critical for binding tat protein. It is therefore reasonably practical to synthesize (chemically or enzymatically) pharmaceutically acceptable nucleic acid or other analogues of this specific binding site which are sufficiently small to be capable of assimilation into cells.

These analogues can then be used as competitive inhibitors of tat protein activity in cells; by removing tat present in the cells, via its reaction with the TAR analogue, viral growth in those cells could be effectively inhibited.

It has been found that tat binding seems to be dependent on the presence of the three unpaired residues, including one uridine (U) residue, which form a bulge near the apex of the stem in the HIV TAR RNA [SEQ ID NO: 1] structure. Tat binding is also dependent on the presence of flanking base pairs that also form part of the tat binding site. Certain mutants in this binding site fail to bind tat in vitro and also fail to trans-activate in vivo. Hence a nucleic acid or other analogue that includes this small region (which has been found to be a high-affinity binding site) can mimic the configuration found in the TAR sequence and can bind to the tat protein.

Hence, the binding sequence in the oligonucleotide(s) of the present invention preferably comprises three unpaired residues including a uridine residue corresponding to $U_{23}$ in the sequence of HIV TAR RNA [SEQ ID NO: 1], as well as flanking base pairs corresponding to $G_{26-C39}$ in the sequence of HIV TAR RNA [SEQ ID NO: 1] that together form the recognition site of the tat protein.

Because such a small region of the TAR is actually needed to bind tat, analogues of the binding site can be constructed which are composed of oligonucleotides of therapeutically useful lengths, preferably (but not limited to) twenty residues or less. Such molecules are more likely to be able to enter infected cells, and hence to be of use in pharmaceuticals for in vivo treatment of HIV infections, than are those of greater length. A molecule in accordance with the invention is preferably in the form of an oligonucleotide(s) less than or equal to twenty residues in length, so as to facilitate assimilation into cells infected with the HIV virus.

Since RNA itself is metabolically unstable in cells, the oligonucleotide(s) used in the present invention is preferably modified in some way so as to increase its stability in the cells. The binding sequence, which is necessarily an RNA sequence, may for instance be incorporated into a DNA basic sequence or some other structurally-related variant oligonucleotide, which basic sequence imparts the necessary metabolic stability to the oligonucleotide(s) as a whole.

Thus any oligonucleotide (or combination of oligonucleotides) which includes the RNA sequence corresponding to the site bound by tat, when introduced into cells, should be capable of binding tat and thus acting as a competitive inhibitor of viral growth within those cells. Indeed, any small molecule which is able to bind to tat at the TAR RNA binding site could be used as an anti-viral agent, and the invention includes within its scope such a molecule for use as an anti-HIV agent. Such a molecule could mimic the shape of the RNA structure in TAR RNA or could contain functional groups equivalent to the RNA structure in TAR RNA.

Since oligoribonucleotides are sensitive to cleavage by cellular ribonucleases, it may be If preferable to use as the competitive inhibitor a chemically modified oligonucleotide (or combination of oligonucleotides) that mimics the action of the RNA binding sequence but is less sensitive to nuclease cleavage. Other modifications may also be required, for example to enhance binding, to enhance cellular uptake, to improve pharmacology or pharmacokinetics or to improve other pharmaceutically desirable characteristics.

The oligonucleotide may be a naturally occurring oligonucleotide, or may be a structurally related variant of such an oligonucleotide having modified bases and/or sugars and/or linkages. The term "oligonucleotide" as used herein is intended to cover all such variants.

Modifications, which may be made either to the binding site per se or to the part of the oligonucleotide not involved in binding, may include (but are not limited to) the following types:
a) Backbone modifications (see FIG. 5 below)
   i) phosphorothioates (X or Y or W or Z=S or any combination of two or more with the remainder as O).
      e.g. Y=S (81), X=S (49), Y and Z=S (45)
   ii) methylphosphonates (eg Z=methyl (69))
   iii) phosphoramidates (Z=N-(alkyl)$_2$ e.g. alkyl methyl, ethyl, butyl) (Z=morpholine or piperazine) (44) (X or W=NH) (64)
   iv) phosphotriesters (Z=O-alkyl e.g. methyl, ethyl etc) (70)
   v) phosphorus-free linkages (e.g. carbamate, acetamidate, acetate) (55, 56)
b) Sugar modifications
   i) 2'-deoxynucleosides (R=H)
   ii) 2'-O-methylated nucleosides (R=OMe) (80)
   iii) 2'-fluoro-2'-deoxynucleosides (R=F) (61)
c) Base modifications—(for a review see 58)
   i) pyrimidine derivatives substituted in the 5-position (e.g. methyl, bromo, fluoro etc) or replacing a carbonyl group by an amino group (75).
   ii) purine derivatives lacking specific nitrogen atoms (e.g. 7-deaza adenine, hypoxanthine) or functionalized in the 8-position (e.g. 8-azido adenine, 8-bromo adenine)
d) Oliizonucleotides covalently linked to reactive functional groups, e.g.:
   i) psoralens (71), phenanthrolines (82), mustards (83) (irreversible cross-linking agents with or without the need for co-reagents)
   ii) acridine (intercalating agents) (57)
   iii) thiol derivatives (reversible disulphide formation with proteins) (48)
   iv) aldehydes (Schiff's base formation)
   v) azido, bromo groups (UV cross-linking)
   vi) ellipticines (photolytic cross-linking) (74)
e) Oligonucleotides covalently linked to lipophilic groups or other reagents capable of improving uptake by cells, e.g.:
   i) cholesterol (63), polyamines (62), other soluble polymers (e.g. polyethylene glycol)
f) Oligonucleotides containing alpha-nucleosides (72)
g) Combinations of modifications a)–f)

Experiments using modified ologoribonucleotides with residues replaced with 4-thio-2'-deoxythymidine have given better binding to tat than comparable unmodified oligoribonucleotides. It is thus preferred to modify the or each oligoribonucleotide by inclusion of one or more 4-thio-2'-deoxythymidine residues.

It should be noted that such modified oligonucleotides, while sharing features with oligonucleotides designed as "anti-sense" inhibitors, are distinct in that the compounds correspond to sense-strand sequences and the mechanism of action depends on protein-nucleic acid interactions and does not depend upon interactions with nucleic acid sequences.

The molecule and the pharmaceutical composition of the present invention may be administered orally, intravenously or by any other suitable method when used to inhibit viral growth in vivo. They may also be used to inhibit viral growth in vitro, for instance in cells in blood which has been removed from a living organism and is later required for transfusion purposes.

The present invention further provides a method of inhibiting growth of HIV virus within cells, comprising the step of administering to the cells a molecule or pharmaceutical composition in accordance with the invention.

The invention also provides a method of treatment of a patient infected with HIV, comprising the step of administering to the patient a molecule or pharmaceutical composition in accordance with the invention.

The invention can also be used as the basis of an assay for identifying compounds that inhibit binding of tat protein to TAR RNA or synthetic analogs thereof, and so have potential use as anti-viral agents.

Thus in a further aspect the invention provides an assay for identifying compounds that inhibit binding of tat protein to TAR RNA, comprising reacting a compound with tat protein and a molecule in accordance with the invention, and determining the degree of binding of tat to the molecule.

By determining the degree of binding of tat to the molecule, and comparing this with results for known standards, an indication can be obtained of the decree of inhibition (competitive or non-competitive) of tat/TAR binding caused by the compound.

The assay is preferably in the form of a filter binding assay, but may also be another type of assay such as a gel mobility-shift assay, a spectroscopic assay, capture assay, etc.

Accurate measurement of the affinity of tat for TAR RNA in the presence of inhibitor molecules, such as competitor molecules that compete for binding to TAR or molecules that inhibit tat binding to TAR non-competitively, cannot be achieved without the formation of stoichiometric complexes between tat protein and TAR RNA, which is now possible in vitro as a result of improvements in the purification of tat protein from *E. coli* and in methods for performing binding assays.

Compounds identified as having an inhibitory effect on tat/TAR binding can then be further investigated for possible use-as an anti-viral agent. The invention can thus enable screening of potential anti-viral compounds.

The present invention will now be described in greater detail, by way of illustration, with reference to the accompanying Figures, of which:

FIG. 3 shows those sequences in HIV-1 TAR-RNA [SEQ ID NO: 1] which are required for the in vivo activity and in vitro binding of tat; HIV-2 TAR [SEQ ID NO: 2]; SSA [SEQ ID NO: 3]; ASS [SEQ ID NO: 4]; SAS [SEQ ID NO: 5]; ANTISENSE [SEQ ID NO: 6]; G→U (loop) [SEQ ID NO: 7]; ΔU (bulge) [SEQ ID NO: 8]; U→G (bulge) [SEQ ID NO: 9]; G28→C28 [SEQ ID NO: 10]; G28→C28, C37→G37 [SEQ ID NO: 11].

Figure 4:
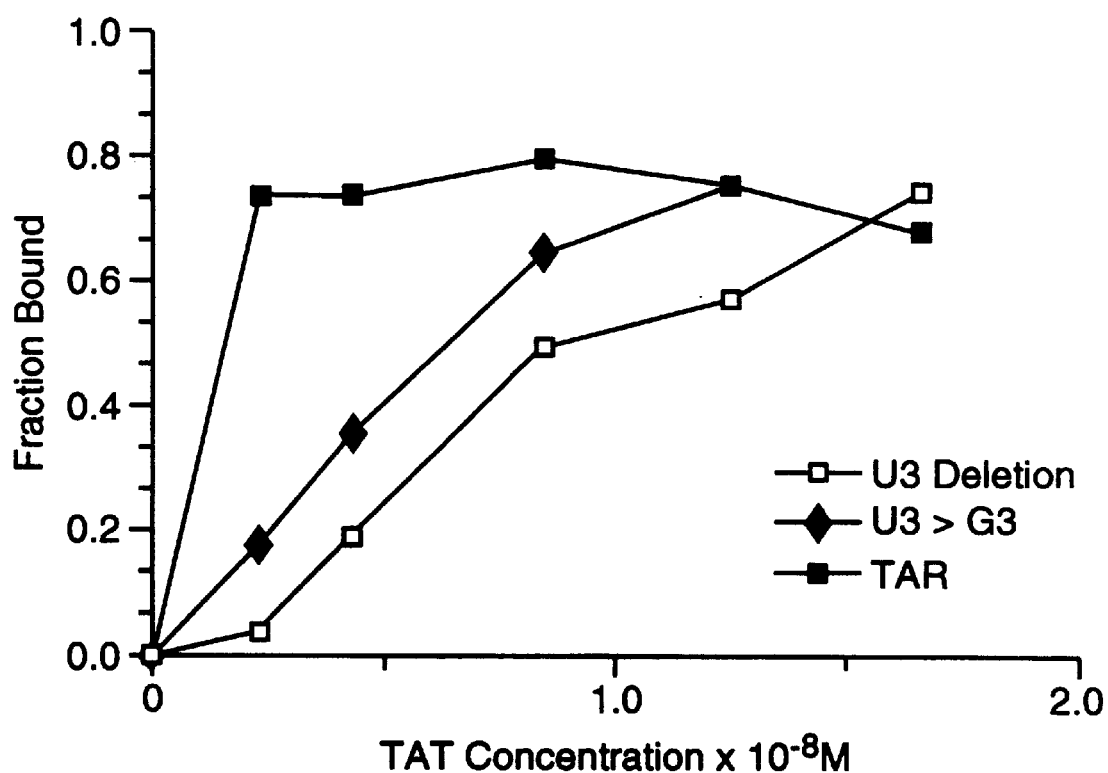

FIG. 4 is a graph of fraction bound versus tat concentration (×10-8 M), illustrating that the uridine-rich bulge ("U-rich bubble") in TAR RNA is essential for tat binding; U3 Deletion [SEQ ID NO: 8]; U3→to G3 [SEQ ID NO: 9]; TAR [SEQ ID NO: 1].

Figure 5:
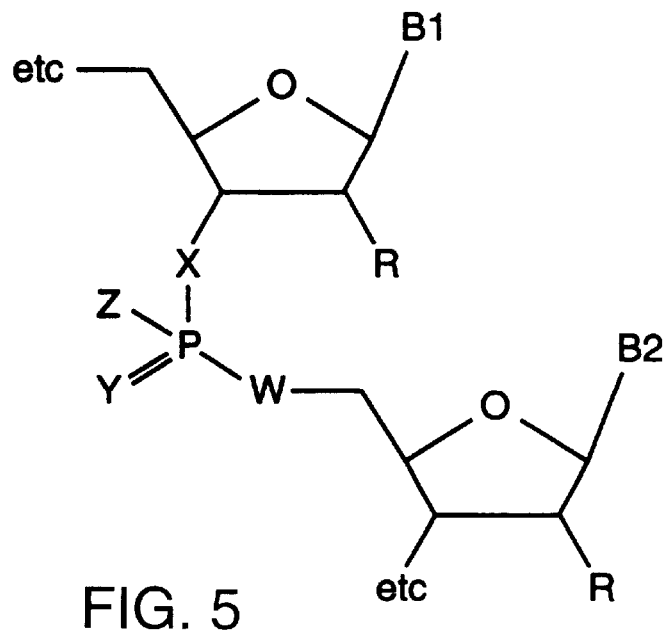
Figure 6:
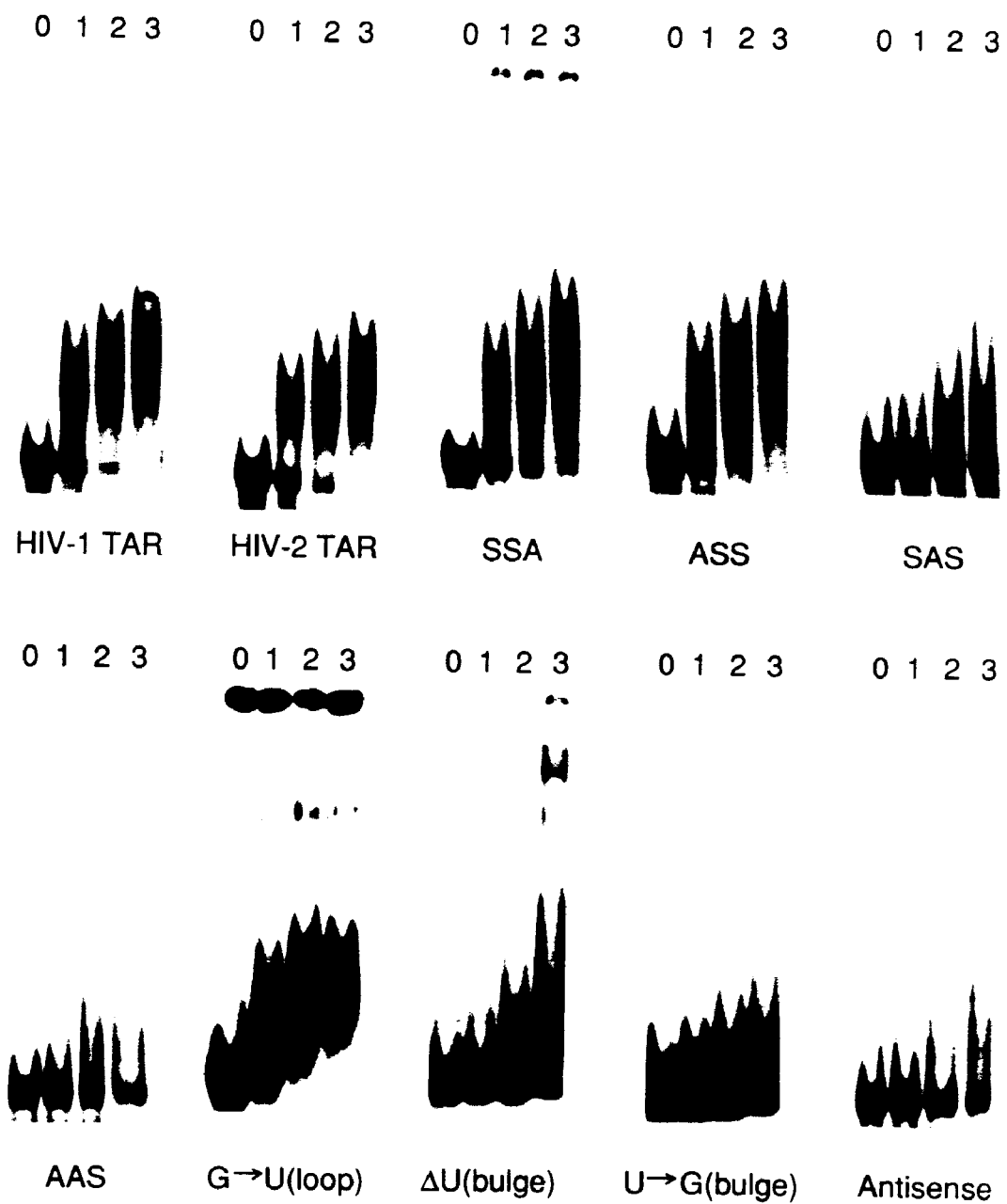

FIG. 5 shows the structures of modified oligonucleotides which might show potential anti-viral activity;

FIG. 6 shows results of gel retardation tat binding assays using various mutant TAR RNA sequences; HIV-1 TAR [SEQ ID NO: 1]; HIV-2 TAR [SEQ ID NO: 2]; SSA [SEQ ID NO: 3]; ASS [SEQ ID NO: 4]; SAS [SEQ ID NO: 5]; G→U (loop) [SEQ ID NO: 7]; ΔU (bulge) [SEQ ID NO: 8]; U→G (bulge) [SEQ ID NO: 9]; antisense [SEQ ID NO: 6].

Figure 7:
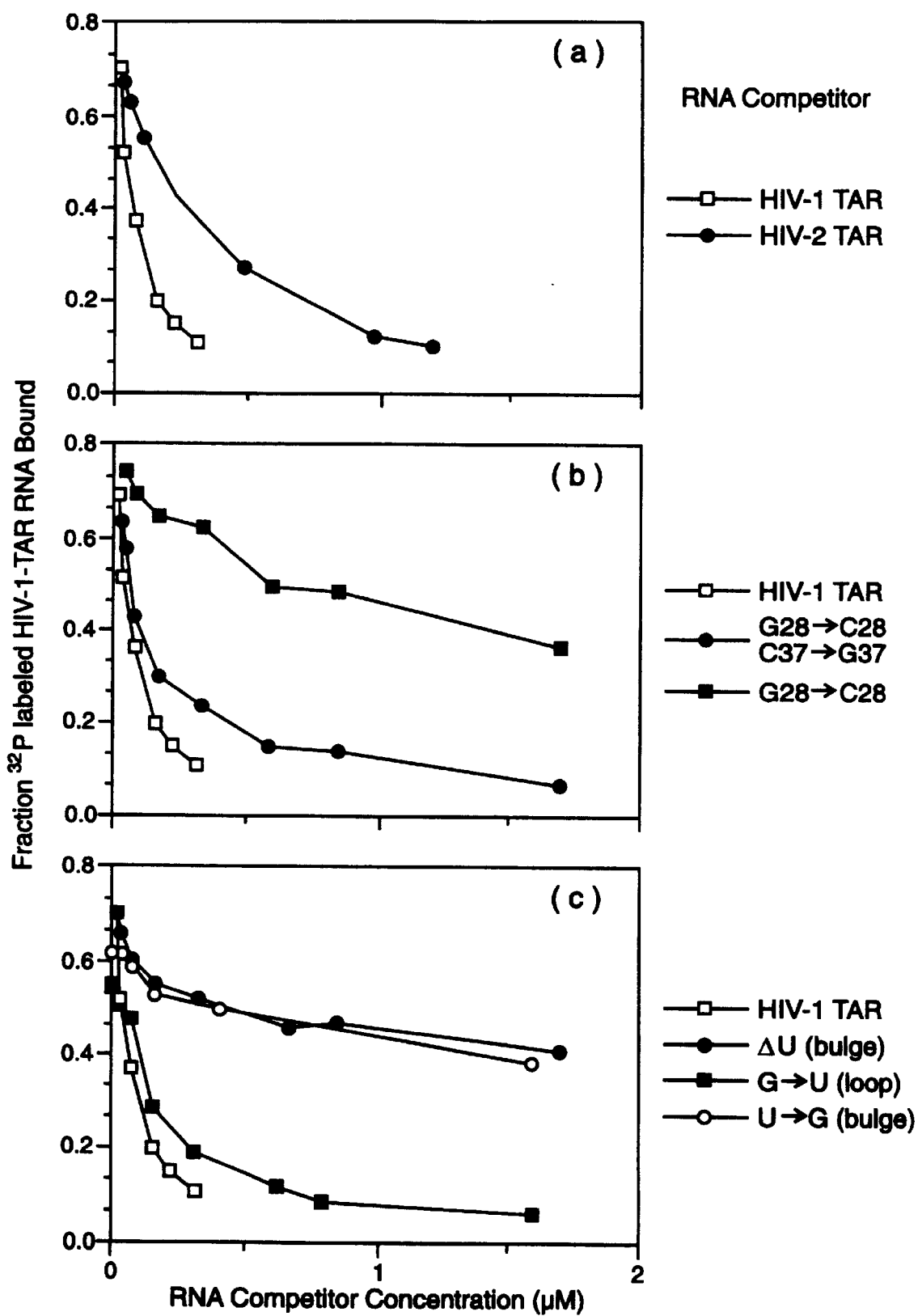

FIG. 7 shows results of filter binding assays using various mutant TAR RNA sequences; in the form of graphs of fraction of $^{32}$P labeled HIV-1 TAR RNA [SEQ ID NO: 1] bound versus RNA competitor concentration (uM); HIV-2 TAR [SEQ ID NO: 2]; G28→C28 [SEQ ID NO: 10]; G28→C28, C37→G37 [SEQ ID NO: 11]; ΔU (bulge) [SEQ ID NO: 8]; G→U (loop) [SEQ ID NO: 7]; U→G (bulge) [SEQ ID NO: 9].

FIG. 8 shows results of transfection experiments using mutant TAR sequences with known affinities for tat, showing the effect of the TAR mutations on transactivation in vivo, in the form of graphs of CAT activity (% acetylation/10 ul extract) versus plasmid DNA (ug); HIV-1 TAR [SEQ ID NO: 1]; G28→C28 [SEQ ID NO: 10]; G28→C28, C37→G37 [SEQ ID NO: 11]; G→U (loop) [SEQ ID NO: 7]; U→G (bulge) [SEQ ID NO: 9]; ΔU (bulge) [SEQ ID NO: 8]; SSA [SEQ ID NO: 3]; ASS [SEQ ID NO: 4]; SAS [SEQ ID NO: 5].

Figure 9A:
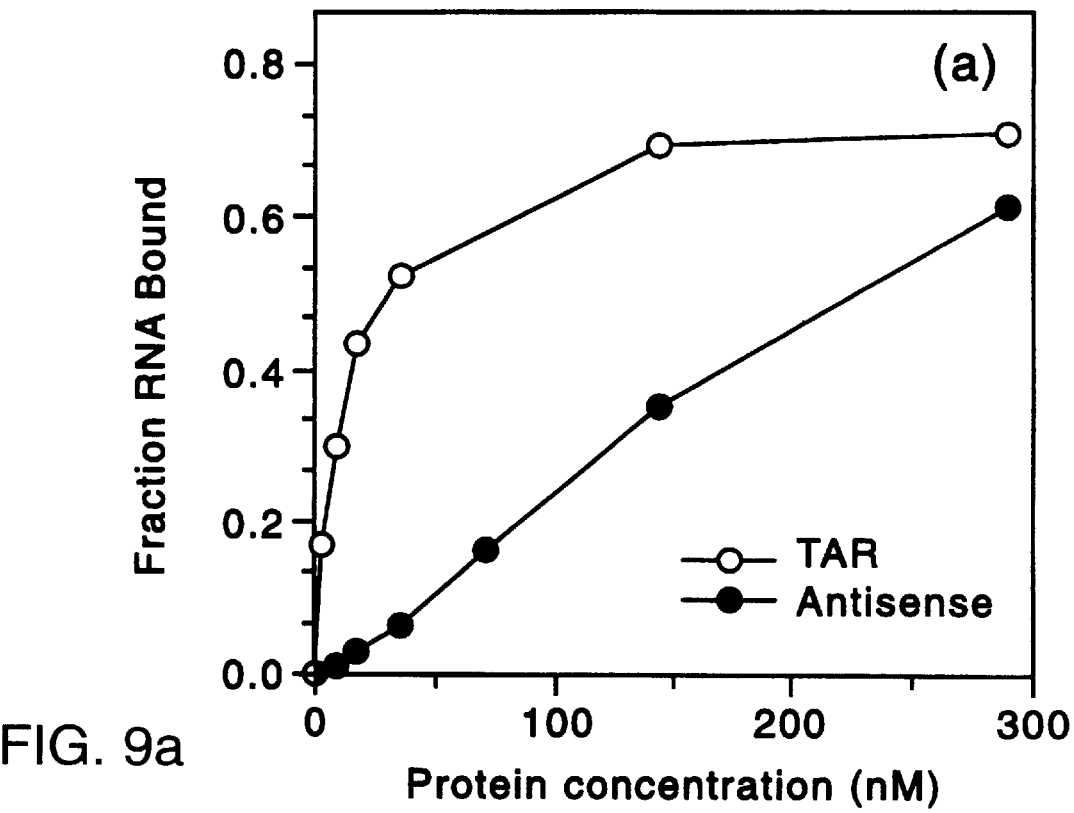
Figure 9B:
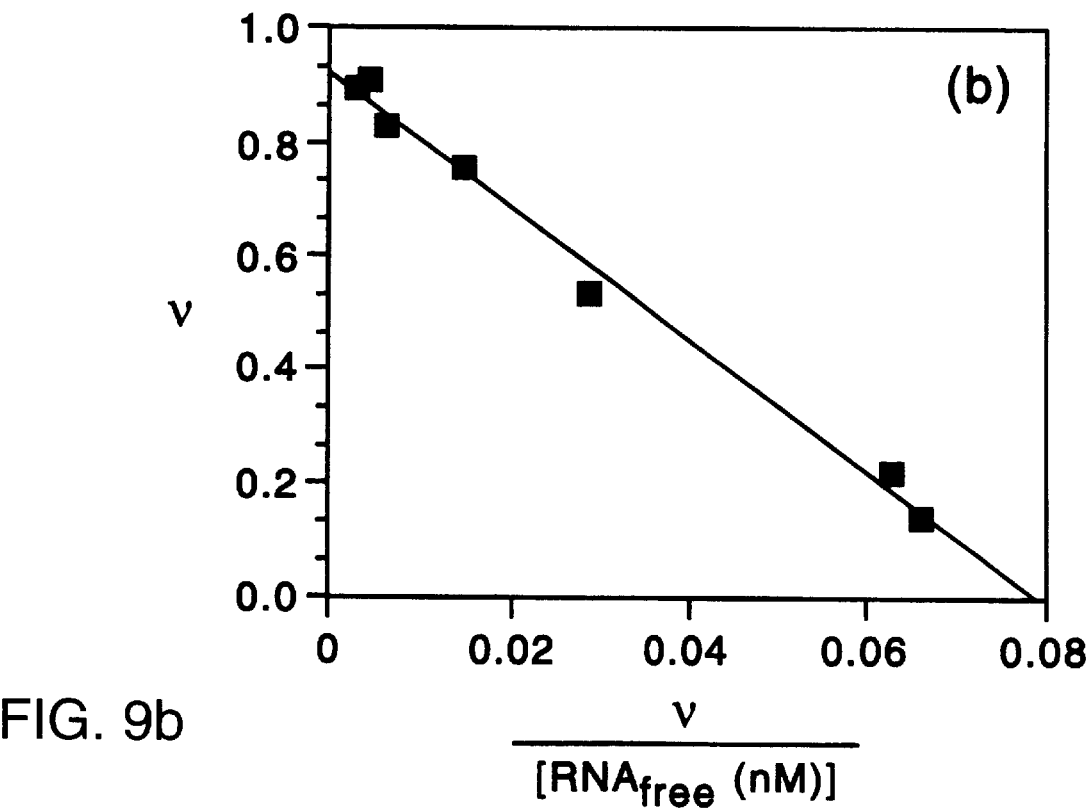

FIG. 9a shows a saturation binding curve of fraction RNA bound versus protein concentration (nM), and FIG. 9b is a Scatchard analysis of tat binding to TAR, used to determine the stoichiometry of the tat/TAR interaction; TAR [SEQ ID NO: 1]; Antisense [SEQ ID NO: 6].

Figure 10:
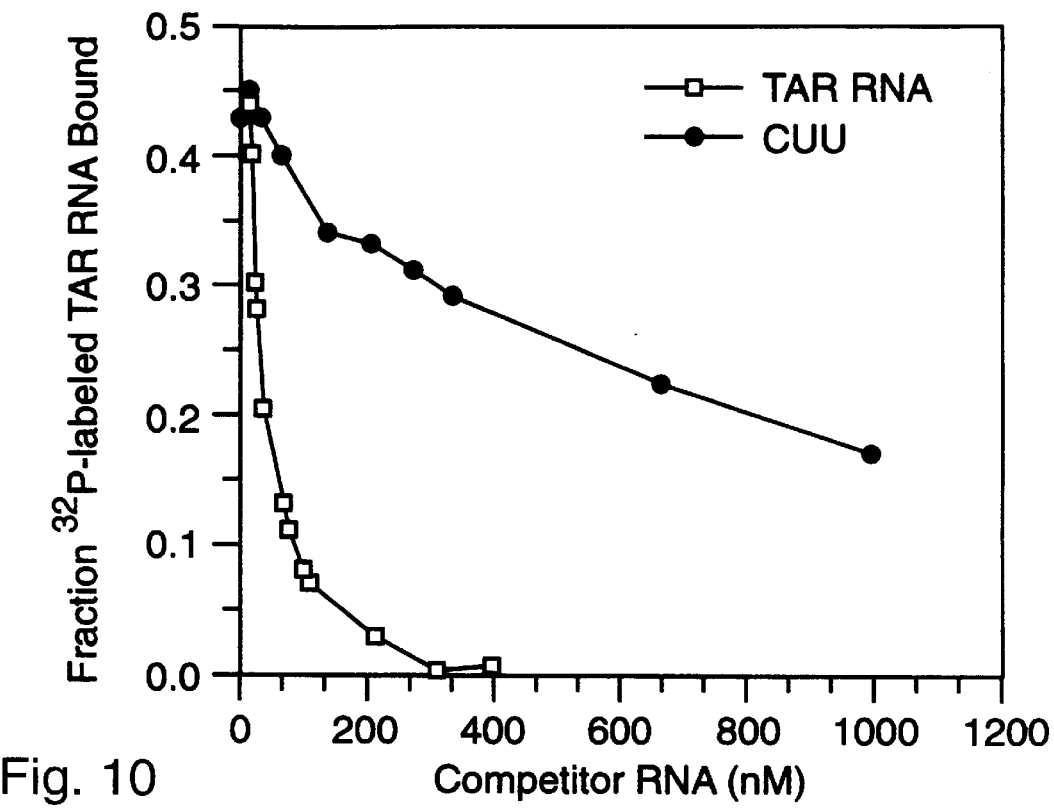
Figure 11:
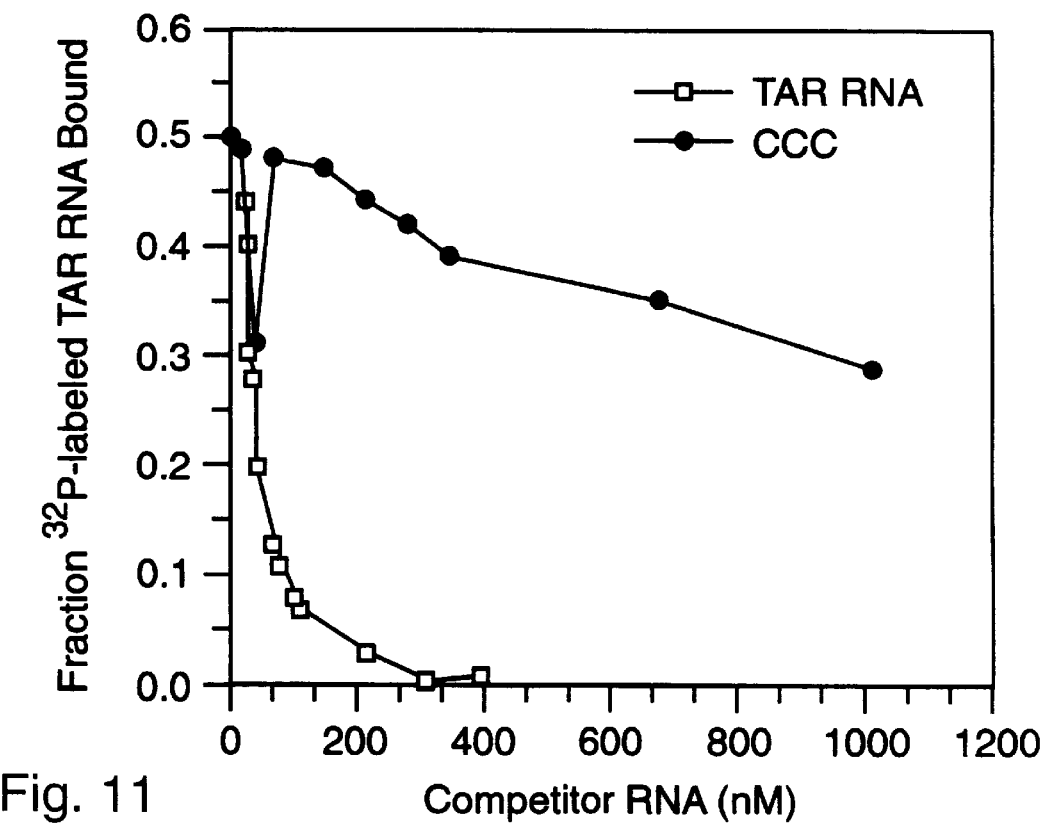
Figure 12:
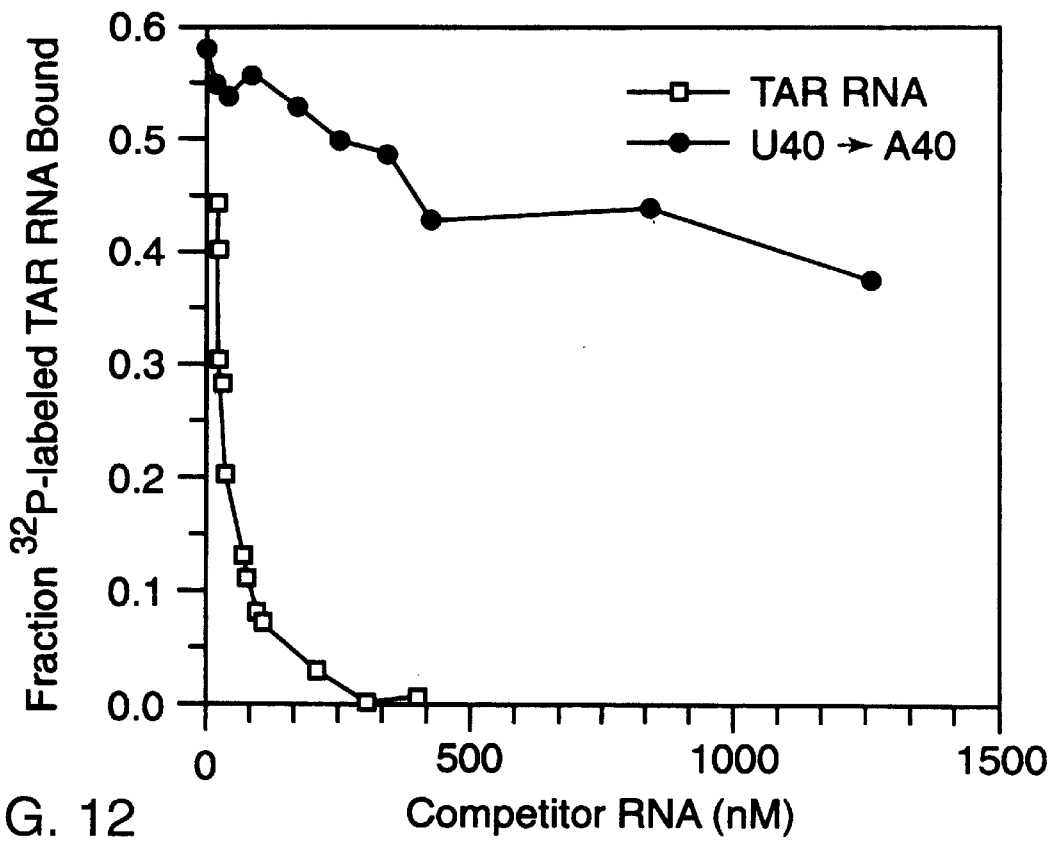
Figure 13:
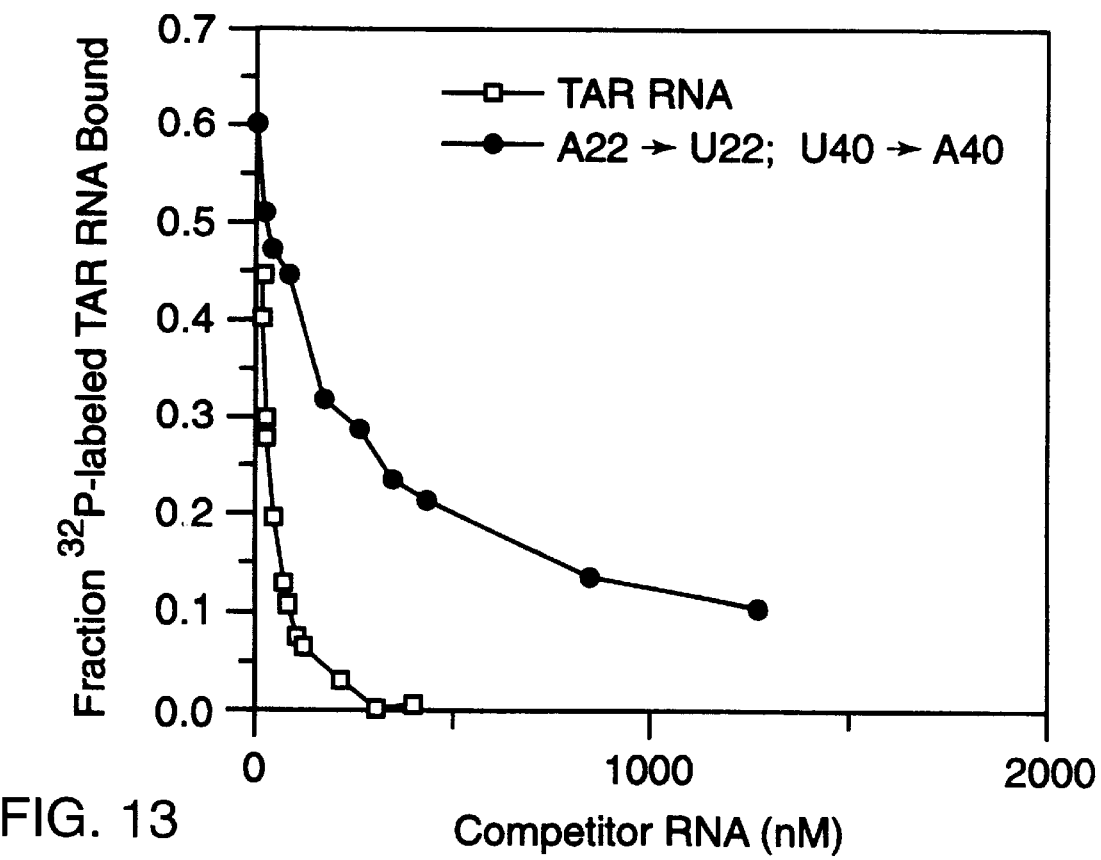
Figure 14:
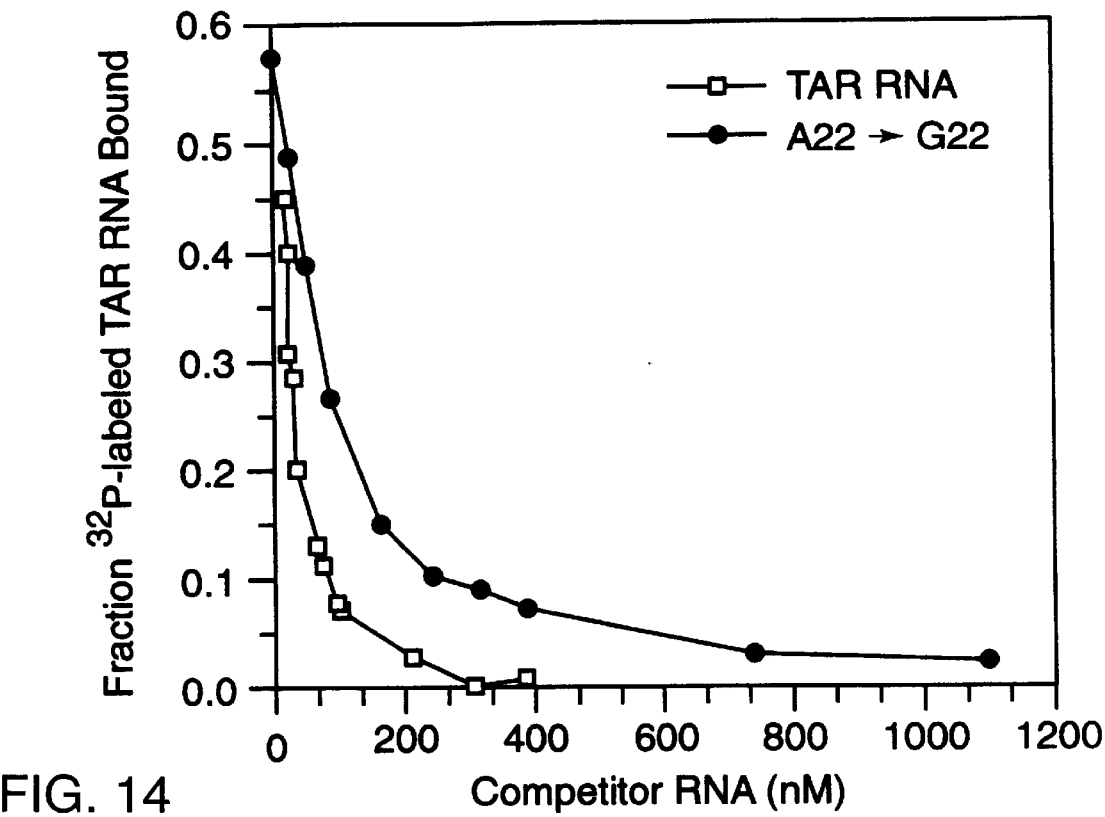
Figure 15:
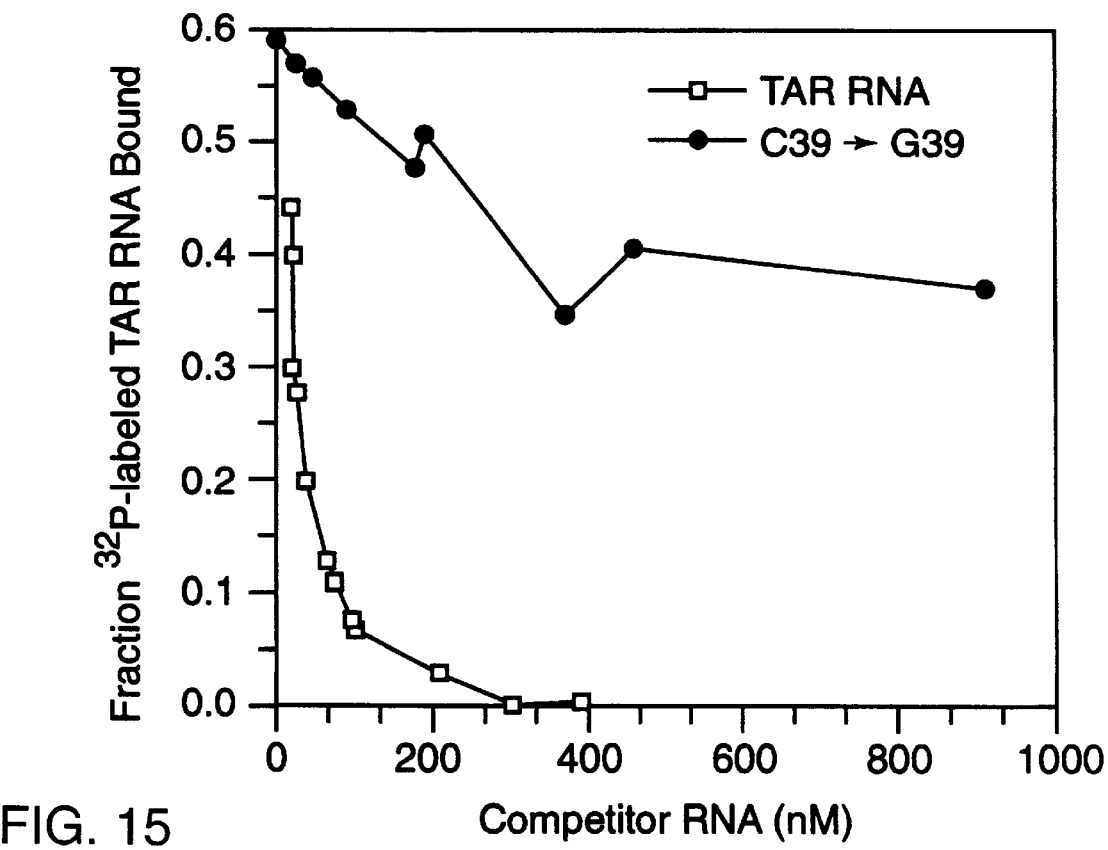
Figure 16:
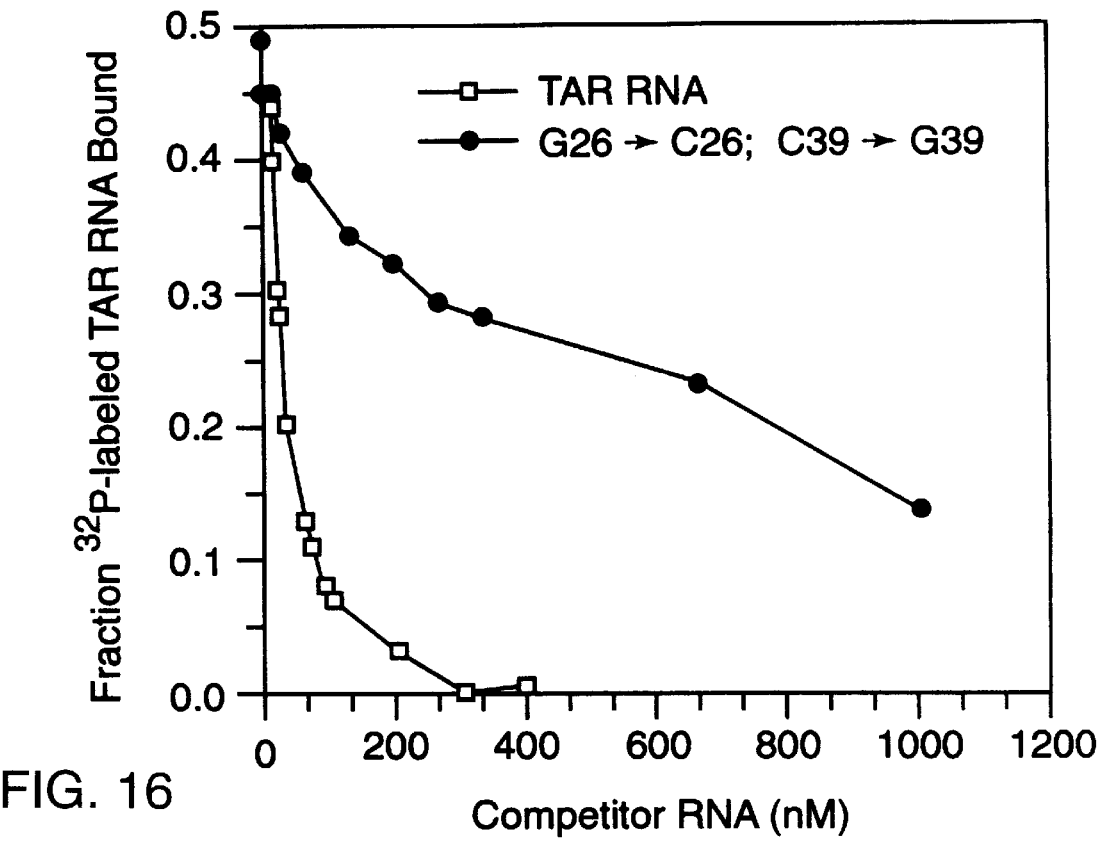
Figure 17:
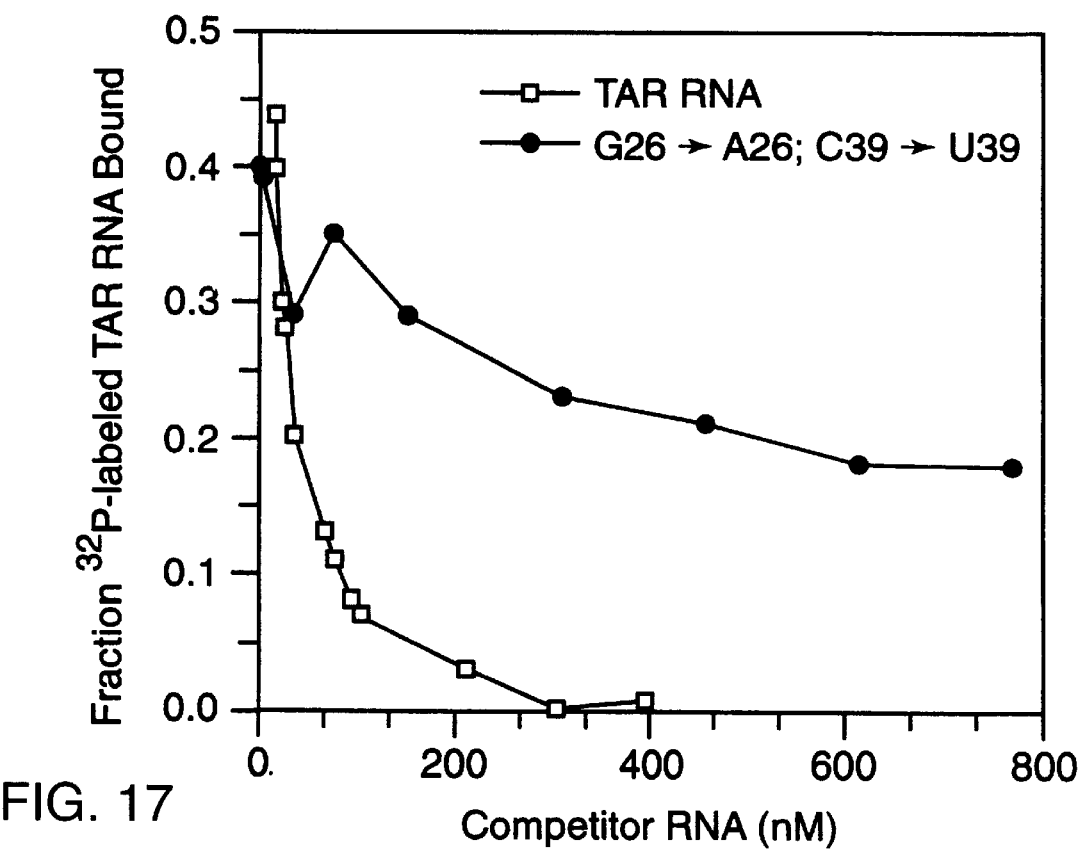
Figure 19:
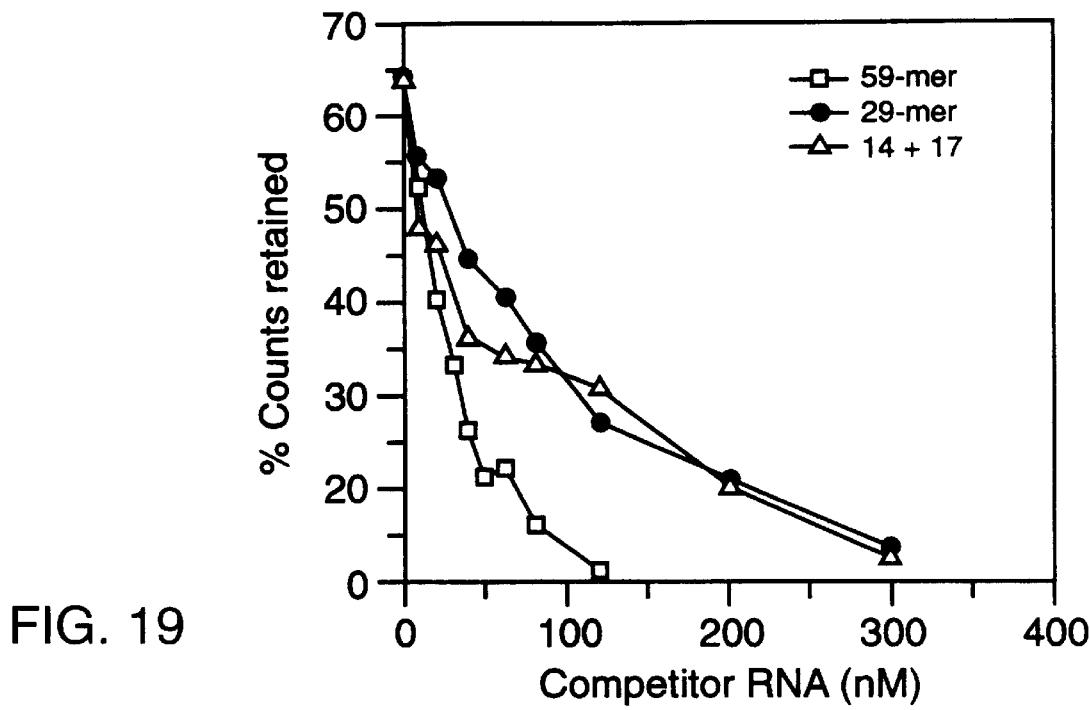
Figure 21:
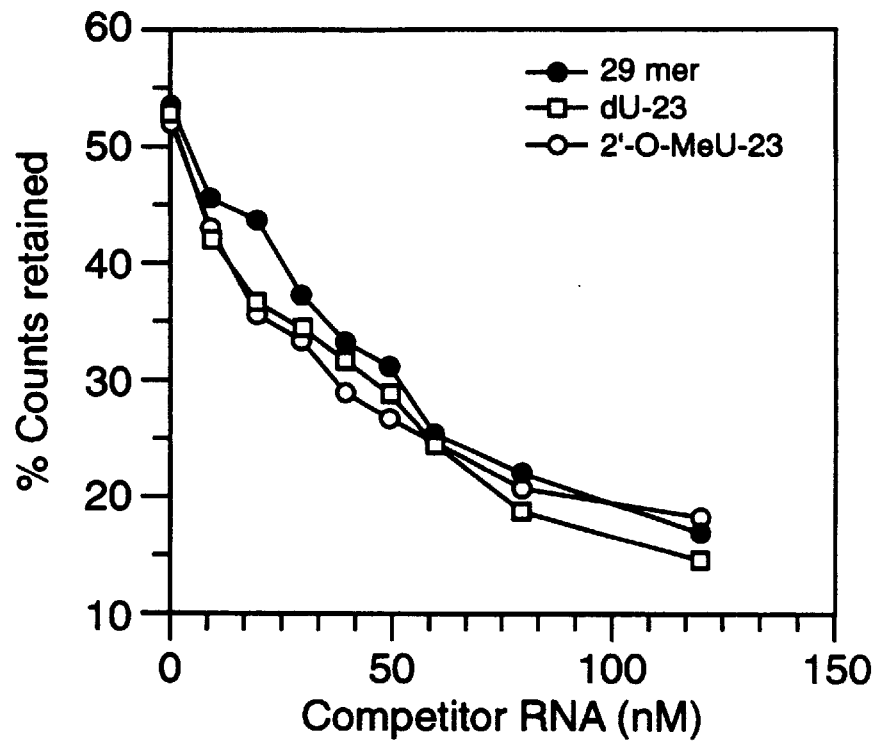
Figure 22:
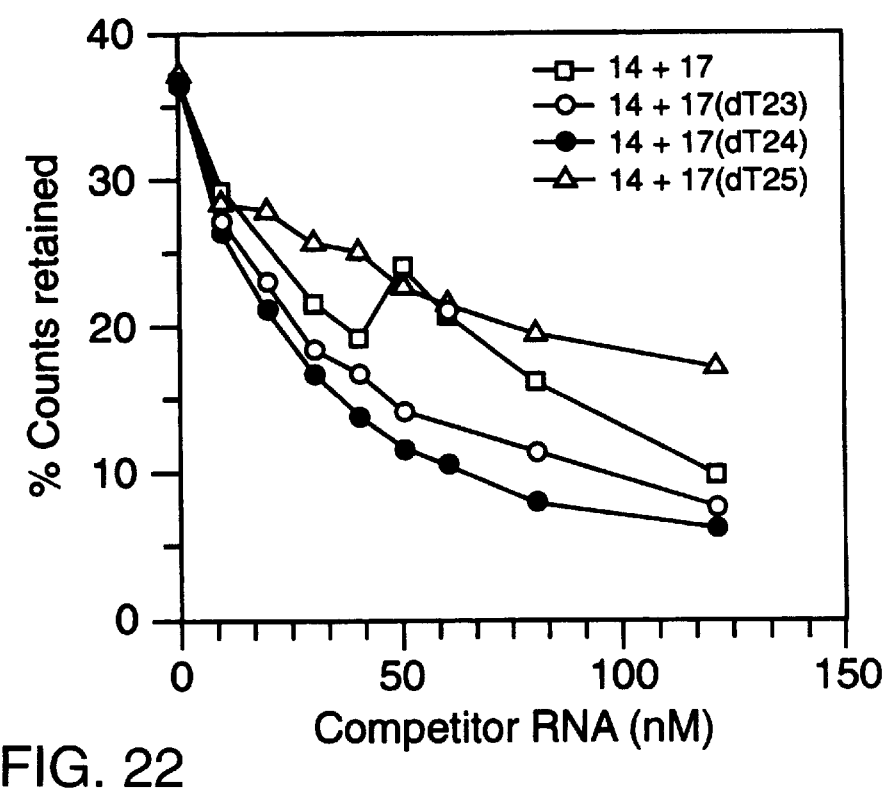
Figure 23:
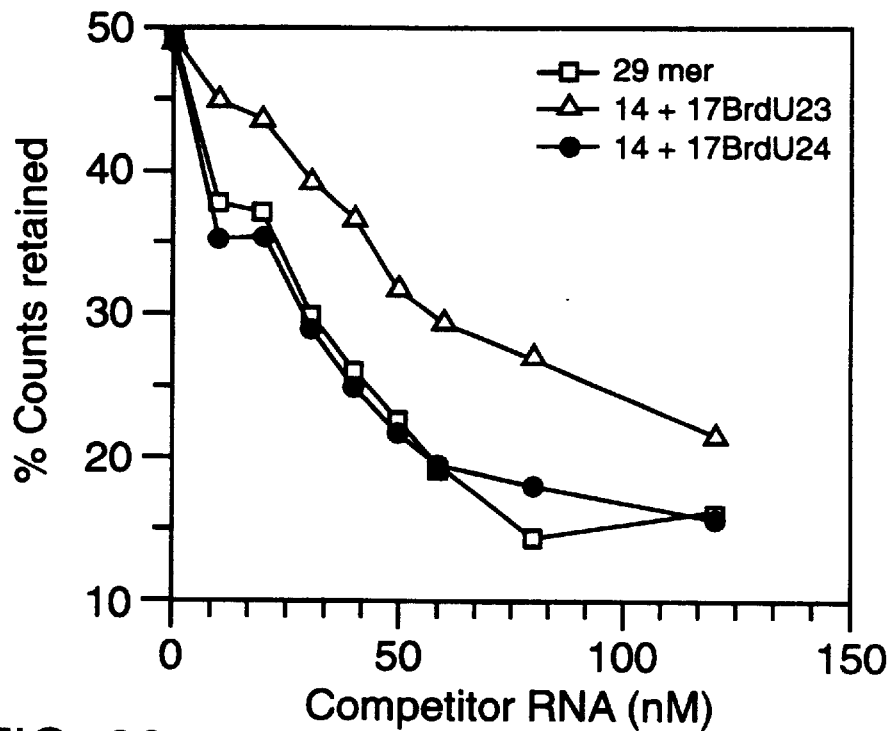
Figure 24:
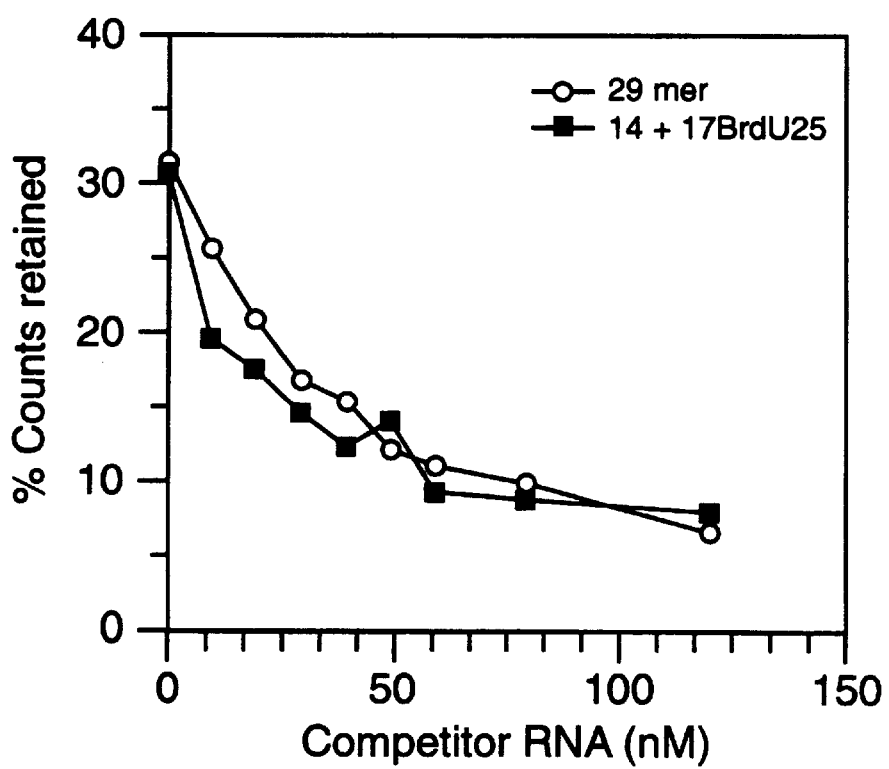
Figure 25:
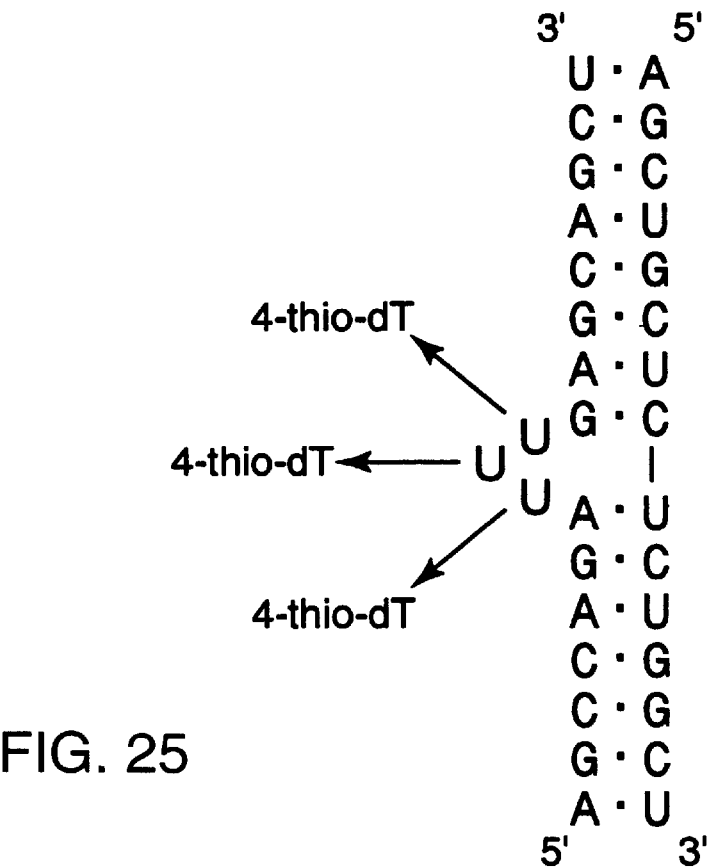
Figure 26:
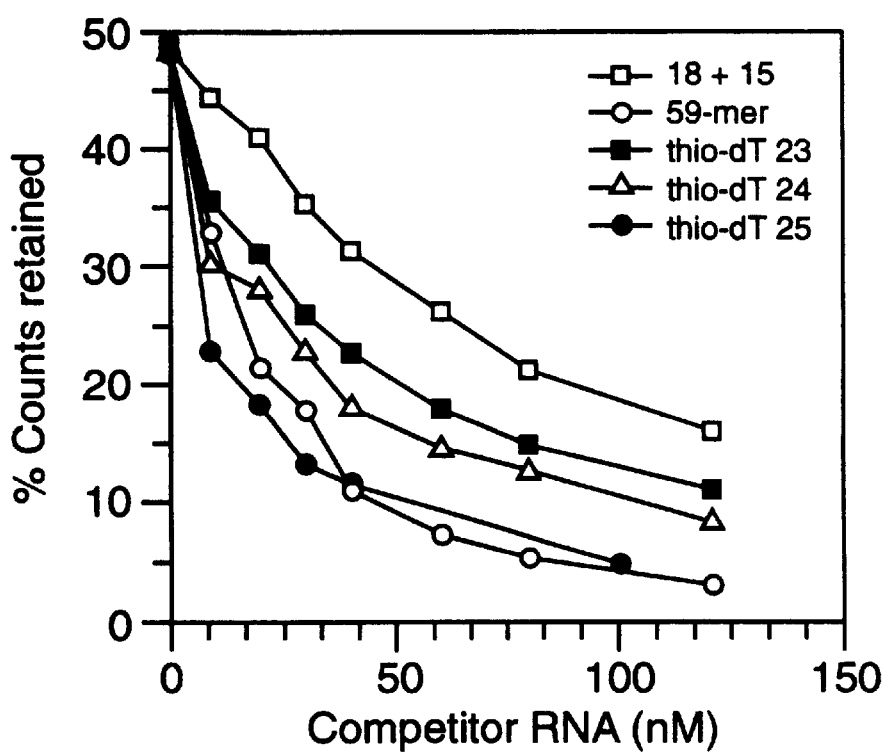

FIG. 10 is a graph of fraction $^{32}$P labeled TAR RNA bound versus competitor RNA (nM), illustrating competition for tat binding between TAR RNA [SEQ ID NO: 1] and a mutant carrying the sequence CUU in the bulge;

FIG. 11 is a graph similar to FIG. 10 illustrating competition for tat binding between TAR RNA [SEQ ID NO: 1] and a mutant carrying the sequence CCC in the bulge;

FIG. 12 is a graph similar to FIG. 10 illustrating competition for tat binding between TAR RNA [SEQ ID NO: 1] and a mutant carrying an A residue at position 40 in the TAR RNA stem;

FIG. 13 is a graph similar to FIG. 10 illustrating competition for tat binding between TAR RNA [SEQ ID NO: 1] and a mutant carrying a U residue at position 22 and an A residue at position 40 in the TAR RNA stem;

FIG. 14 is a graph similar to FIG. 10 illustrating competition for tat binding between TAR RNA [SEQ ID NO: 1] and a mutant carrying a G residue at position 22 in the TAR RNA stem;

FIG. 15 is a graph similar to FIG. 10 illustrating competition for tat binding between TAR RNA [SEQ ID NO: 1] and a mutant carrying a G residue at position 39 in the TAR RNA stem;

FIG. 16 is a graph similar to FIG. 10 illustrating competition for tat binding between TAR RNA [SEQ ID NO: 1] and a mutant carrying a C residue at position 26 and a G residue at position 39 in the TAR RNA stem;

FIG. 17 is a graph similar to FIG. 10 illustrating competition for tat binding between TAR RNA [SEQ ID NO: 1] and a mutant carrying an A residue at position 26 and a U residue at position 39 in the TAR RNA stem;

FIG. 18 shows the RNA sequences of a) full length 59-mer TAR transcript [SEQ ID NO: 1], b) chemically synthesized 29-mer [SEQ ID NO: 12] corresponding to the top part of TAR, c) 14 [SEQ ID NO: 14, nucleotides 2–15] and 17 [SEQ ID NO: 13, nucleotides 1–17] long chemically synthesized oligonucleotides which when annealed form the U-rich bulge and flanking base-pairs representing the tat binding site;

FIG. 19 is a graph of % counts retained versus competitor RNA (nM) showing the results of a competition filter binding assay, demonstrating that chemically synthesized 29-mer [SEQ ID NO: 12] or duplex RNA formed from chemically synthesized 17-mer [SEQ ID NO: 13, nucleotides 1–17]+14-mer [SEQ ID NO: 14, nucleotides 2–15] in each case competes for binding to tat almost as well as a 59-mer RNA transcript synthesized enzymatically;

FIG. 20 shows the RNA sequences of a) chemically synthesized 29-mer where $U_{23}$ has been substituted by either 2'-deoxyuridine (dU) [SEQ ID NO: 15] or by 2'-O-methyluridine (2'O-MeU) [SEQ ID NO: 16] and b) chemically synthesized 17-mer annealed to 14-mer to form a duplex RNA where $U_{23}$ or $U_{24}$ or $U_{25}$ has been substituted by 2'-deoxythymidine (dT) [SEQ ID NO: 17, 18 or 19, respectively] or by 5-bromo-2'-deoxyuridine (BrdU) [SEQ ID NO: 20, 21 or 22, respectively];

FIG. 21 is a graph similar to FIG. 19 showing the results of a competition filter binding assay, demonstrating that chemically synthesized 29-mer substituted at $U_{23}$ by either dU [SEQ ID NO: 15] or by 2'-O-MeU [SEQ ID NO: 16] in each case competes for tat binding as well as unmodified 29-mer [SEQ ID NO: 12];

FIG. 22 is a graph similar to FIG. 19 showing the results of a competition filter binding assay, demonstrating that a duplex RNA consisting of a 14-mer [SEQ ID NO: 14, nucleotides 2–15] annealed to 17-mer substituted at a $U_{23}$ [SEQ ID NO: 17] or at $U_{24}$ [SEQ ID NO: 18] by dT in each case competes for tat binding as well as unmodified duplex but a duplex substituted at $U_{25}$ [SEQ ID NO: 19] by dT competes less well compared to unmodified duplex;

FIG. 23 is a graph similar to FIG. 19 showing the results of a competition filter binding assay, demonstrating that a duplex RNA consisting of a 14-mer [SEQ ID NO: 14, nucleotides 2–15] annealed to a 17-mer substituted at $U_{23}$ [SEQ ID NO: 20] by BrdU competes for tat binding less well but that substituted at $U_{24}$ [SEQ ID NO: 21] competes as well compared to unsubstituted duplex;

FIG. 24 is a graph similar to FIG. 19 showing the results of a competition filter binding assay, demonstrating that a duplex RNA consisting of a 14-mer [SEQ ID NO: 14, nucleotides 2–15] annealed to a 17-mer substituted at $U_{25}$ by BrdU [SEQ ID NO: 22] competes for tat binding as well compared to unsubstituted duplex;

FIG. 25 shows 15 [SEQ ID NO: 14] and 18-long chemically synthesized oligonucleotides which when annealed form duplex RNA containing a U-rich bulge but where $U_{23}$ [SEQ ID NO: 23], $U_{24}$ [SEQ ID NO: 24] or $U_{25}$ [SEQ ID NO: 25] is replaced in each case by 4-thio-2'-deoxythymidine; and FIG. 26 is a graph similar to FIG. 19 showing the results of a competition filter binding assay, demonstrating that a duplex RNA consisting of a 15-mer [SEQ ID NO: 14] annealed to a 18-mer substituted at either $U_{23}$ [SEQ ID NO: 23], $U_{24}$ [SEQ ID NO: 24] or $U_{25}$ [SEQ ID NO: 25] by 4-thiodT in each case competes for binding better than unsubstituted duplex. 4-ThiodT substituted $U_{25}$ [SEQ ID NO: 25] analogue competes as well as unmodified 59-mer [SEQ ID NO: 1].

DETAILED DESCRIPTION OF THE FIGURES

FIG. 1.

The mechanism of HIV-1 gene expression is shown schematically. In a newly infected cell, binding of cellular transcription factors to the long terminal repeat (LTR) stimulates a basal level of transcription of the early mRNAs encoding tat, rev and nef shown at (1). As tat levels rise in the cell, transcription is stimulated by the trans-activation mechanism. This leads to increased production of the early mRNAs and accumulation of partially spliced or unspliced RNA transcripts in the nucleus (2). As rev levels rise in the cell, RNAs carrying the rev-responsive element are exported from the nucleus. These act as mRNAs for the structural proteins encoded by gag, pol and env. The full-length HIV transcript acts both as a mRNA for gag-pol and as the virion RNA (3).

FIG. 2.

Figure 1:
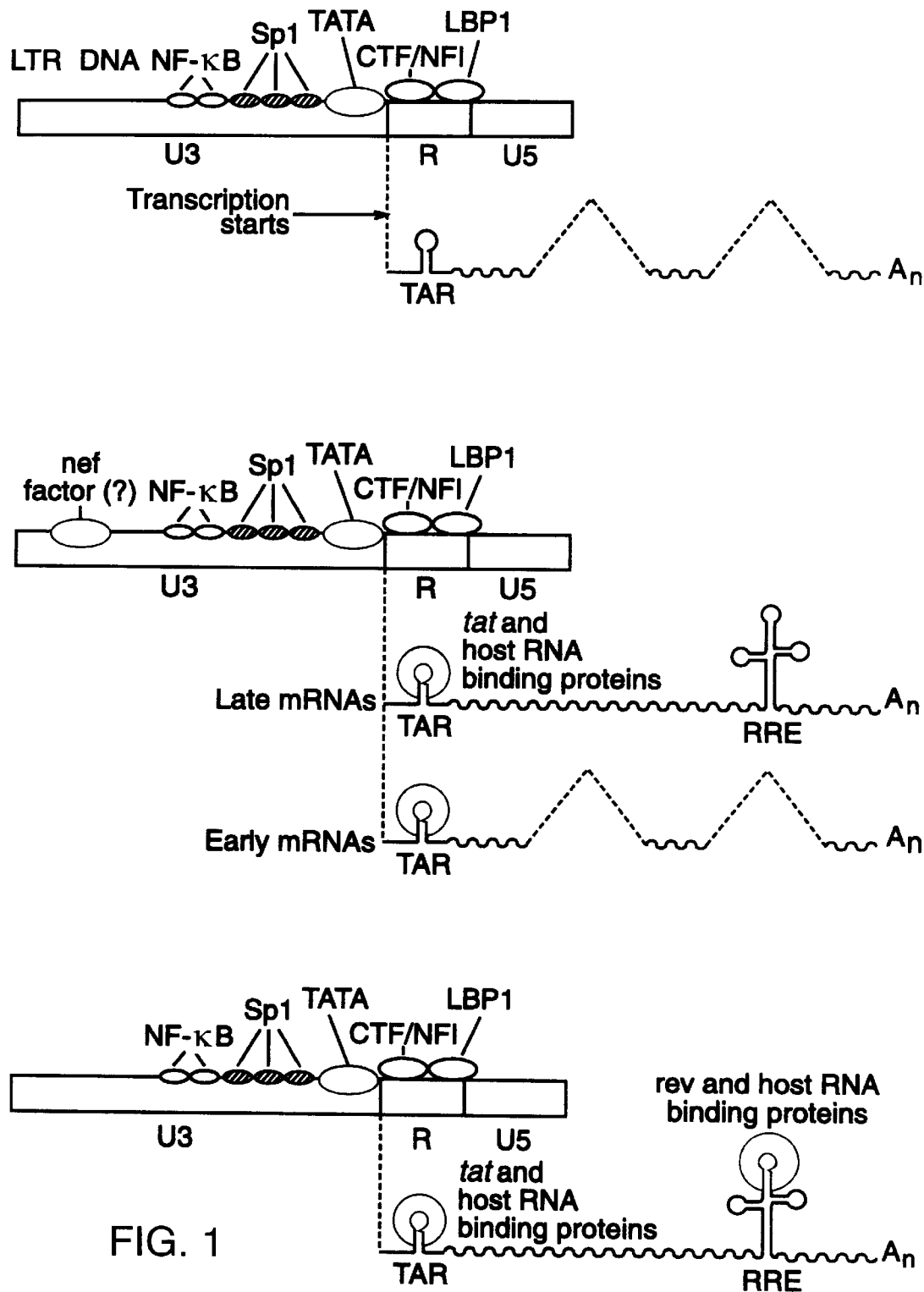
FIG. 1 illustrates the genetic elements and cellular factors controlling HIV-1 gene expression.
Figure 2B:
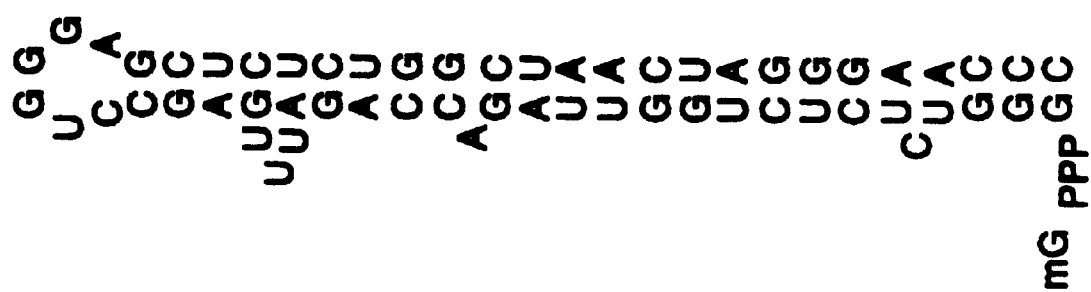
FIG. 2 shows how the RNA-binding proteins tat and rev control HIV-1 gene expression; TAR [SEQ ID NO: 1] and RRE [SEQ ID NO: 26] are shown.
Figure 2C:
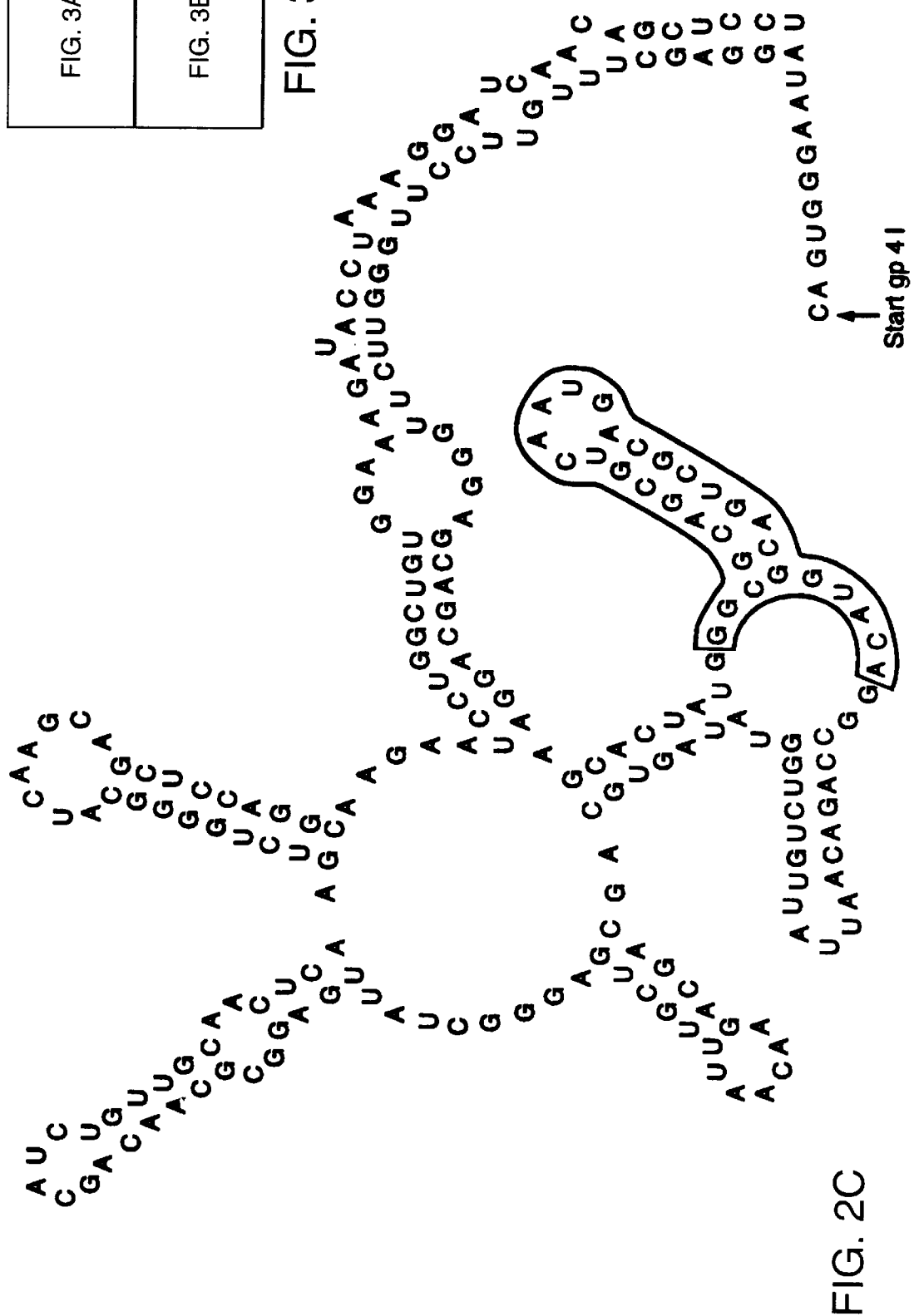

Positions and sequences of regulatory RNA for tat (TAR [SEQ ID NO: 1], trans-activation responsive region, FIG. 2B) and for rev (RRE [SEQ ID NO: 26], rev-responsive region, FIG. 2C) are shown below the HIV genetic map (FIG. 2A).

FIG. 3.

Figure 3A:
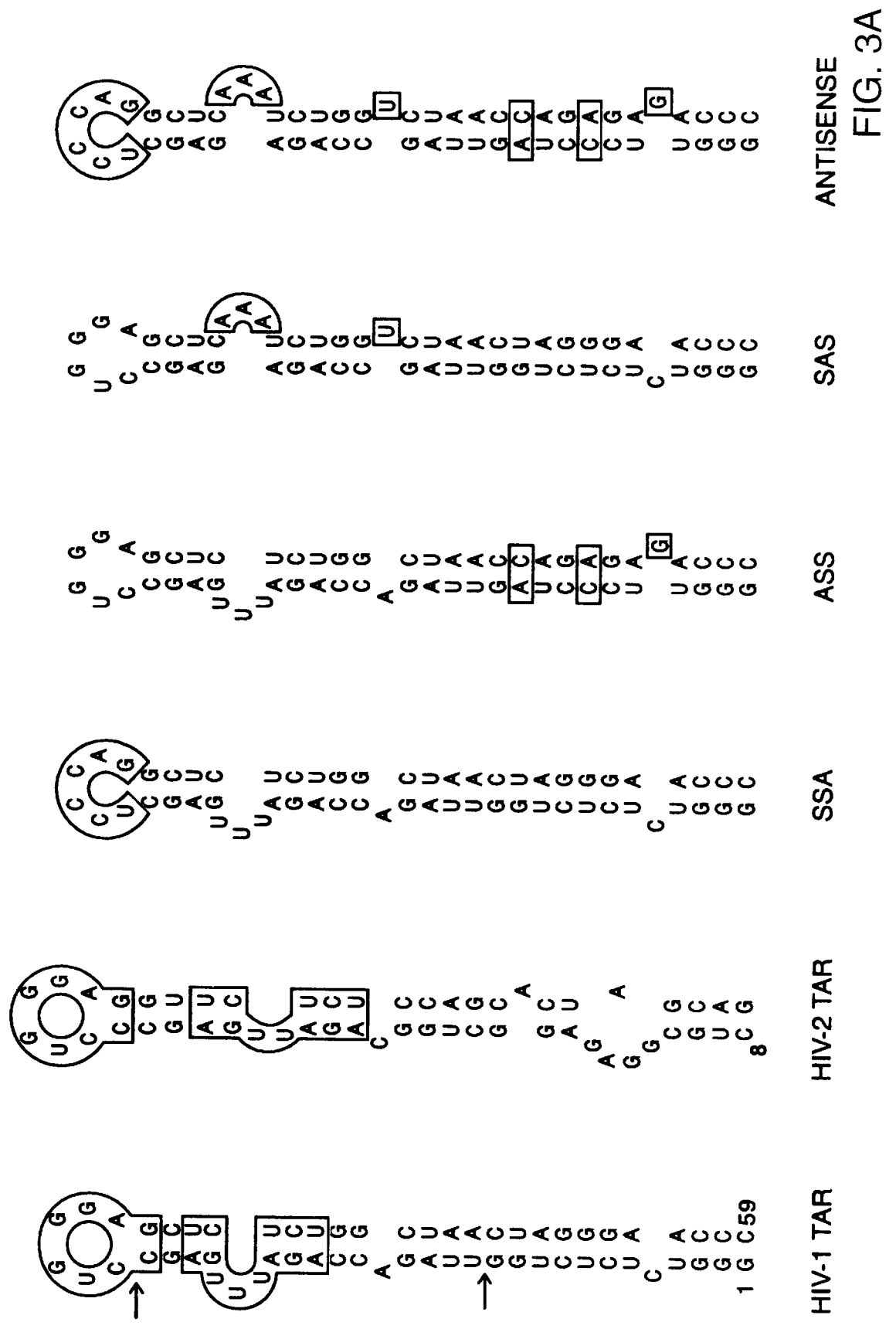

Recent studies of mutants which alter the structure of the TAR region suggest strongly that the TAR RNA sequence [SEQ ID NO: 1, FIG. 3A] must be transcribed in the nucleus and correctly folded in order for trans-activation to occur. The TAR RNA sequence adopts a stable, nuclease-resistant, stem-loop structure (5). Two notable features in this structure are the loop sequence (residues 30–35), and the "bulge" created by three non-base paired residues (residues 23–25) located near the tip of the double-helical stem. Both the bulge and loop sequences in TAR are conserved between HIV-1 [SEQ ID NO: I] and HIV-2 [SEQ ID NO: 2, FIG. 3A] (8, 9) and both regions are present in the minimal functionally active TAR sequence located between nucleotides +19 and +42 (5, 10–14).

In order to map precisely the recognition site for tat on TAR, the ability of purified tat protein expressed in *E. coli* (6, 94) to bind transcripts containing HIV-1 TAR mutations was studied. Previous experiments had shown that the antisense TAR RNA [SEQ ID NO: 6, FIG. 3A] sequence fails to bind tat (6), although this sequence differs from TAR at only 15 positions (see FIG. 3A). To assess the contribution of each of these sequence alterations to tat binding to TAR, a series of TAR molecules was constructed, having sense or antisense sequences in either the loop, the upper stem or the lower stem as well as a series of mutations in the stem or loop structures (FIG. 3). HIV-1 tat is able to trans-activate LTRs carrying the first stem-loop of HIV-2 TAR [SEQ ID NO: 2] (20, 25). Since the two TAR sequences are not closely related (8, 9) and only residues in the loop and bulge regions are conserved, it was also of interest to determine whether this sequence could bind HIV-1 tat.

Figure 3B:
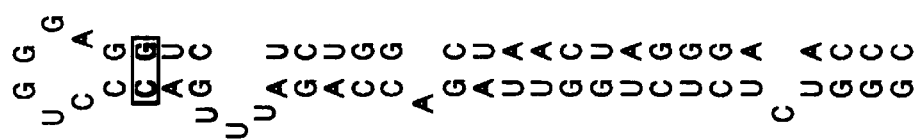
Figure 3B:
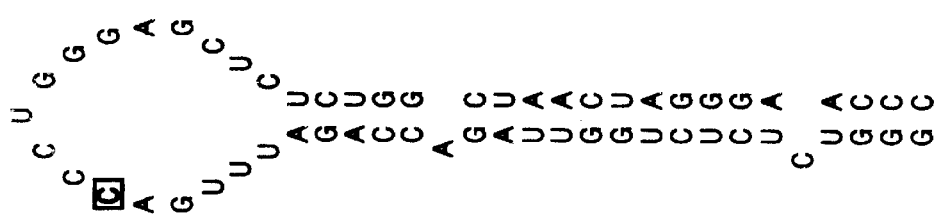
Figure 3B:
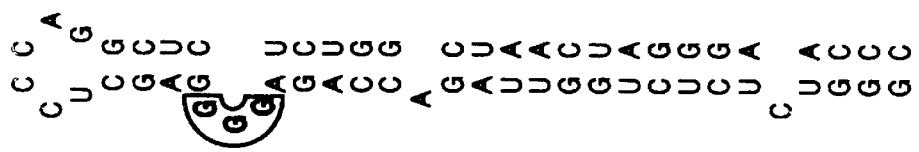
Figure 3B:
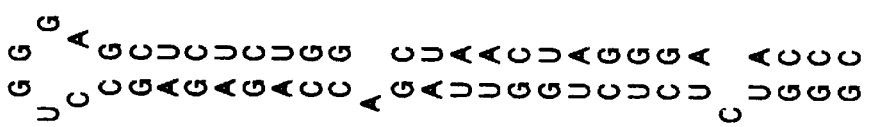
Figure 3B:
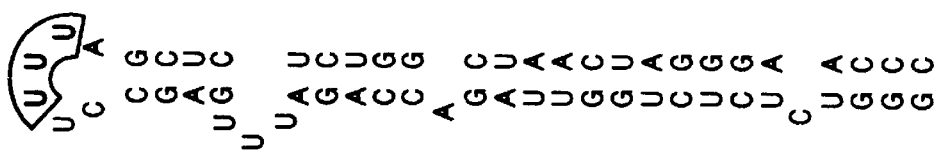

In FIGS. 3A and 3B, which shows TAR RNA sequences and proposed secondary structures, numbering is relative to the capped G residue at position +1. Proposed secondary structures are based on previous analysis of TAR RNA (5). Conserved sequence features present in both HIV-1$_{BRU}$ TAR [SEQ ID NO: 1] and HIV-2$_{ROD}$ TAR [SEQ ID NO: 2] are boxed and shaded. Sequences in the antisense sequence [SEQ ID NO: 6] to HIV-1 TAR that differ from the sense sequence are boxed. Arrows denote points of division of the RNA structure into lower stem, upper stem (including the U-rich bubble) and the loop. SSA: sense stem, antisense loop sequence [SEQ ID NO: 3, FIG. 3A]. ASS: anti-sense lower stem, sense upper stem and loop sequences [SEQ ID NO: 4, FIG. 3A]. SAS: anti-sense upper stem flanked by sense lower stem and loop sequences [SEQ ID NO: 5, FIG. 3A]. Antisense: anti-sense sequence to HIV-1$_{BRU}$ TAR [SEQ ID NO: 6, FIG. 3A]. G3 to U3 (loop): residues 32–34 are changed to uridine (U) [SEQ ID NO: 7, FIG. 3B]. Delta U3 (bulge): residues 23–25 are deleted [SEQ ID NO: 8, FIG. 3B]. U3 to G3 (bulge): residues 23–25 are changed to Guanine (G) [SEQ ID NO: 9, FIG. 3B]. $G_{28}$ to $C_{28}$ [SEQ ID NO: 10, FIG. 3B] point mutation expected to disrupt the top of the TAR stem/loop structure. $G_{28}$ to $C_{28}+C_{37}$ to $G_{37}$ [SEQ ID NO: 11, FIG. 3B]: pair of point mutations expected to have a normal TAR stem/loop structure.

FIG. 4.

Studies at the Laboratory of Molecular Biology (Cambridge) have shown that the HIV-1 tat protein binds specifically to HIV-1 TAR RNA [SEQ ID NO: 1] in gel-retardation, filter-binding and immunoprecipitation assays with an apparent dissociation constant of 12 nM (6, 94).

HIV-l tat also binds specifically to HIV-2 TAR [SEQ ID NO: 2] sequences (see below, and FIGS. 6 and 7). Since the only regions of homology shared between the HIV-1 [SEQ ID NO: 1] and HIV-2 TAR [SEQ ID NO: 2] sequences are residues in the loop region and a short region of the stem containing the U-rich bubble, it follows that the tat binding site is located within one of these regions.

A series of mutations altering residues in each of these sequences was prepared. Tat binding in vitro is dependent upon the presence of an intact U-rich region sequence, but is largely independent of the loop.

The results shown graphically in FIG. 4 are from experiments in which binding reactions (500 ul) contained 40 nMolar$^{32}$ P uniformly radiolabelled TAR RNA at a specific activity of 100,000 Ci/mole; 0.5 ug calf thymus DNA; 0.2 ug yeast TRNA; 40 units RNAsin (Promega); 50 mm Tris-HCl pH 7.9 and 20 mM KCl. Reaction mixtures were set up on ice and increasing amounts of HIV-1 tat protein were added and the reaction mixtures were filtered through prewashed nitrocellulose filters (Millipore 0.45 uM pore size). The filters were dried and counted by liquid scintillation counting. The fraction of radiolabelled RNA bound was plotted against HIV-1 tat concentration.

TAR [SEQ ID NO: 1]: Wild type TAR RNA (HIV$_{BRU}$ sequence).

U3 deletion [SEQ ID NO: 8]: A TAR RNA sequence in which the three uridine (U) bases (residues 23–25) are deleted.

U3 to G3 [SEQ ID NO: 9]: A TAR RNA sequence in which the three uridine (U) bases (residues 23–25) are changed to guanine (G).

FIG. 5 shows the structure of an oligonucleotide which could be of use in the synthesis of such RNA fragments. Modifications to the oligonucleotide, in order to decrease its sensitivity to nuclease cleavage or otherwise to increase its stability, may include alterations to the structures of the bases B1 and B2, the sugar backbone R or the phosphate linkages W,X,Y and Z, as described above.

FIGS. 6 and 7 show results of gel retardation and filter binding assay experiments respectively, demonstrating binding of HIV-1 tat to the first stem-loop structure in HIV-2 TAR RNA [SEQ ID NO: 2]. The methods used and results obtained are outlined below.

i) Gel retardation assays (FIG. 6)
Method

RNA transcripts were prepared by transcription with either T3 or T7 RNA polymerases of TAR regions residues +1 to +57, cloned between the HindIII and EcoRI sites of the Bluescribe M13+ expression vector (Stratagene). RNA transcripts corresponding to HIV-1 TAR [SEQ ID NO: 1], SSA [SEQ ID NO: 3], SAA and SAS [SEQ ID NO: 5] were synthesized from clones linearized with EcoRI and transcribed with T3 RNA polymerase. RNA transcripts corresponding to the antisense HIV-1 TAR [SEQ ID NO: 1], AAS, ASS [SEQ ID NO: 4], and ASA (not shown) sequences were prepared from the same plasmids linearized with HindIII and transcribed using T7 RNA polymerase. All other RNA molecules were synthesized using T3 RNA polymerase following EcoRI cleavage of the plasmid vector. The RNA products each carry 13 nucleotides of vector sequence at their 5' end and four nucleotides at their 3' ends. These sequences do not influence the binding of tat to TAR (6). Transcription mixtures contained 1 ug linearized plasmid, 40 mM Tris-HCl pH 8.0, 10 mM MgCl 2, 2 mM Spermidine-HCl, 50 mM NaCl, 100 uM each ribonucleotide triphosphate, 40 uCi (alpha-$^{32}$P) UTP (410 Ci/m mol) and 10 units of RNA polymerase in a final volume of 30 ul and were incubated at 37° C. for 30 minutes. After phenol extraction and precipitation from ethanol the RNA was purified from a 9% polyacrylamide denaturing gel. The specific activity of the RNA product was determined and appropriate amounts were used in binding assays. Binding reaction mixtures (15 ul) contained 1 ng of uniformly labeled RNA probe, 0.5 ug calf thymus DNA, 0.2 ug yeast TRNA, 40 units RNAsin (Promega), 50 mM Tris-HCl and 20 mM KCl and 0 to 600 ng tat protein, prepared from E. coli beta-galactosidase-tat fusion proteins, as described previously (6). After incubation at either 30° C. or 4° C. for 10–20 minutes, the reaction mixtures were applied to a 6% non-denaturing polyacrylamide gel (Acrylamide: Bis, 40:0.5) in 3.3 mM sodium acetate, 6.7 mM Tris (adjusted to pH 7.9 with HCl). The gel buffer was recirculated during electrophoresis at 35 mA for approximately 2 hours at room temperature. Gels were dried and exposed to X-ray film at −80° C. using intensifying screens.

Results

The autoradiographs of FIG. 6 show discrete complex formation between tat and $^{32}$ P-labeled RNA transcripts of HIV-1 TAR [SEQ ID NO: 1], HIV-2 TAR [SEQ ID NO: 2], SSA [SEQ ID NO: 3], ASS [SEQ ID NO: 4], and G to U (loop) [SEQ ID NO: 7]. No complexes were formed with the SAS [SEQ ID NO: 5], AAS, delta U3 (bulge) [SEQ ID NO: 8], U to G (bulge) IF [SEQ ID NO: 9] or antisense sequences. Numbers above each gel lane refer to ul of HIV-1 tat protein at 200 ng/ul added to each reaction mixture. The RNA sequences are as shown in FIG. 3.

Gel retardation (FIG. 6) and filter binding assays (data not shown) using the sense/antisense chimeras have also shown that tat binding to TAR is always dependent upon the presence of a sense sequence in the upper region of the stem but not in the loop. Thus the mutants ASS [SEQ ID NO: 4], SSA [SEQ ID NO: 3] and ASA each bind tat with wild-type affinities, while each of the mutants SAS [SEQ ID NO: 5], AAS and SAA bind tat with significantly reduced affinities and fail to form complexes in the gel retardation assay (FIG. 6). This is further evidence for the supposition that the tat binding site must be located in the upper stem region of TAR (FIG. 3).

ii) Filter binding assays (FIG. 7)

Improvements in the binding assay have allowed for the formation of complexes between tat and TAR RNA [SEQ ID NO: 1] using nearly equimolar concentrations of protein and RNA. In these assays TAR mutants which show reduced binding to tat are also poor competitive inhibitors of tat binding to wild-type RNA sequences. For example, in competition binding assays a TAR mutant in which each of the three U residues in the U-rich bubble is replaced by G residues has an apparent $K_d$ of 240 nM.

Method

Competitor RNA was produced by transcription of 100 ug of the appropriate DNA template in a 2.5 ml reaction mixture containing 40 mM Tris-HCl pH 7.6, 25 mM NaCl, 16 mM $MgCl_2$, 10 mM dithiothreitol and 100 ug pure T3 RNA polymerase. The polymerase enzyme was produced by over-expression in E. coli BL21 using the plasmid (pCM 56) (26). Binding reactions (500 ul) were set up on ice and contained 80 pM $^{32}$P-labeled TAR RNA (17,600 dpm, 200 uCi/n mol) and unlabeled TAR RNA to give a final concentration of 20 nM, 0.5 ug calf thymus DNA, 0.2 ug yeast tRNA, 40 units RNAsin (Promega), 50 mM Tris HCl and 20 mM KCl. After addition of competitor RNA, binding was initiated by addition of HIV-1 tat protein to a final concentration of 400 ng/ml (40 nM). The binding reaction mixtures were then filtered under reduced pressure through prewashed nitrocellulose filters (Millipore 0.45 uM pore size) and filters were dried and counted by liquid scintillation counting.

Results

The graphs shown in FIG. 7 illustrate competition for tat binding between TAR RNA [SEQ ID NO: 1] and the various mutant TAR sequences. Numerical data are given in Table 1. The fraction of $^{32}$P-labeled TAR RNA bound was plotted against the final concentration of competitor RNA. The sequence of TAR and the various TAR mutants used in this experiment are as shown in FIG. 3. In these experiments reactions included 20 nM TAR and 40 nM tat protein and increasing amounts of unlabeled competitor RNA from 40 nm to 6 uM. The graphs do not include data obtained with competitor RNA concentrations greater than 2 uM. Assuming an equimolar ratio of tat and TAR in the complex and $K_d$=12 nM, as measured in direct filter binding assays, 70% of the input TAR RNA is expected to be retained on filters in the absence of competitor RNA. In theory, 40 nM tat will bind 50% of the input TAR RNA ($D_{1/2}$) when the total TAR RNA concentration is 56 nM. This value is in good agreement with the measured value for $D_{1/2}$, of 64 nM TAR (panel a). TAR mutants which bind tat with low affinity are poor competitors and give higher values for $D_{1/2}$.

TAR RNA sequences which are poorly bound by tat are also correspondingly poor competitive inhibitors of binding in solution. The affinity of tat for HIV-2 TAR [SEQ ID NO: 2] measured in direct binding assays ($K_{d=30}$ nM—Table 1), or in the competition binding assays (FIG. 7a and Table 1, $D_{1/2}$=160 nM), was approximately 2.5-fold lower than for HIV-1 TAR [SEQ ID NO: 1]. Replacement of the U residues in the bulge with G residues [SEQ ID NO: 9] abolished tat binding to TAR in gel retardation assays (FIG. 6) and produced a dramatic reduction in tat affinity, $D_{1/2}$=400 nm, $K_d$ greater than 100 nM (FIG. 7c and Table 1). Deletion of the U-rich bulge [SEQ ID NO: 8] also abolished tat binding to TAR in gel retardation assays (FIG. 6) and increased $D_{1/2}$ to 290 nM, $K_d$ greater than 70 nM. In contrast, replacement of the three G residues in the loop sequence with U residues [SEQ ID NO: 7], produced an RNA molecule which can bind tat with nearly the wild-type affinity, $D_{1/2}$=66 nM, $K_d$ 25 nM (FIGS. 6 and 7c and Table 1). Replacement of $G_{28}$ with a C residue [SEQ ID NO: 10] is expected to destabilize the stem between the U-rich bulge and the loop (FIG. 3). This mutant failed to bind to tat in gel retardation assays (FIG. 6) or to compete efficiently (FIG. 7b and Table 1, $D_{1/2}$=680 nM, K 100 nM), but binding was restored by the compensating greater than second mutation C37 to G37 [SEQ ID NO: 11] (FIG. 7b and Table 1, $D_{1/2}$=76 nM, $K_d$=24 nM).

Competition experiments were not performed using the TAR sense/antisense chimeras [SEQ ID NO: 3–5], because TAR RNA anneals readily at room temperature with antisense RNA to produce a stable duplex with a mobility in polyacrylamide gels similar to that of the tat/TAR complex (data not shown). This hybridization reaction is expected to interfere with protein binding to TAR.

FIG. 8

Figure 8A:
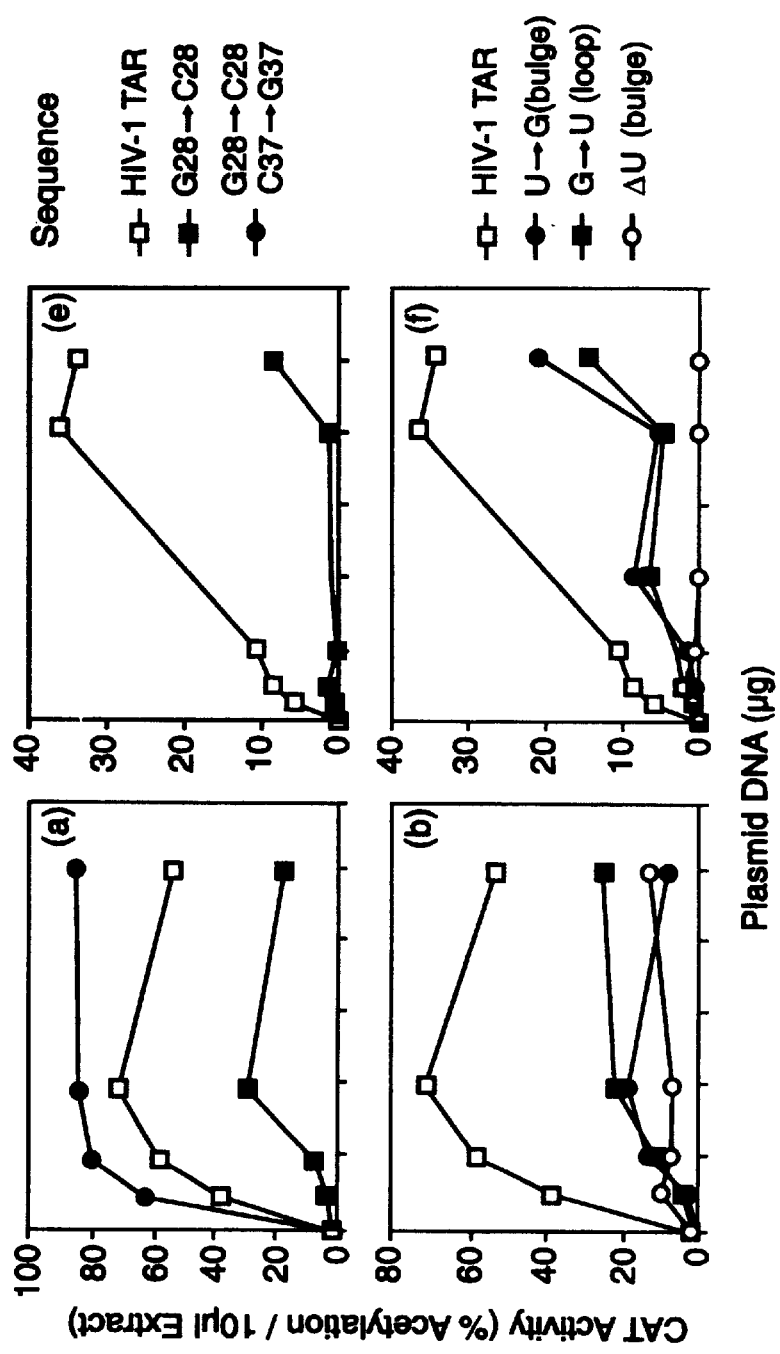
Figure 8B:
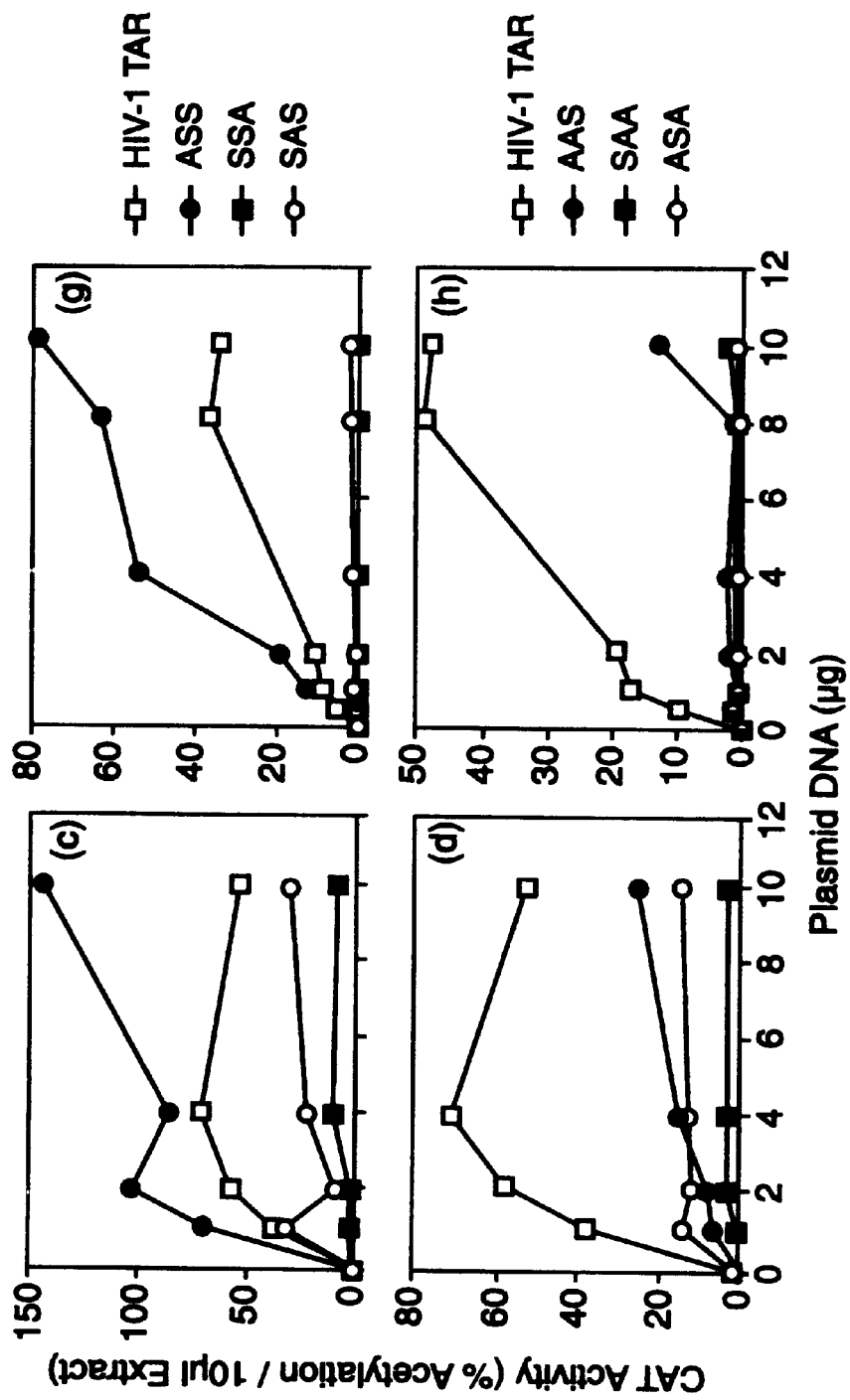

If tat binding to TAR is necessary for trans-activation, then viral LTRs carrying TAR sequences with low affinities for tat should always have reduced tat-dependent promoter activity in vivo. Site-directed mutagenesis experiments on TAR have shown that trans-activation requires sequences in both the U-rich bulge (10, 11) and the loop sequence (12, 27, 28). These observations have now been extended, using TAR mutations with known affinities for tat in transfection experiments, the results of which are shown in FIG. 8. The experiments used either HeLa cells (FIGS. 8a–d) or a constitutive producer of tat, HeLa/C63/tat cells (FIGS. 8e–f).

The TAR sequences depicted in FIG. 3 [SEQ ID NO: 1–11] were introduced into a test plasmid, pD5-3-3, which carries a LTR and approximately 300 bases of 5' flanking sequences derived from the infectious proviral clone NL4 (29). The bacterial chloramphenicol acetyltransferase (CAT) gene and SV40 intron and terminator sequence from pSV2-CAT (30) was inserted downstream of TAR by cloning into the HindIII site at +77. Trans-activation was measured either by cotransfection of HeLa cells with the test plasmids and the tat expression plasmid pC63-4-1 (6) (panels a–d in FIG. 10), or by transfection of the test plasmids alone into HeLa/C63/tat (clone 9) cells (panels e–h).

In these experiments, cells were plated at a density of $3\times10^5$ in a T25 flask and transfected by the calcium phosphate method (31). Transfections in HeLa cells used 8.0 ug of test plasmid, 1.0 to 10 ug of pC63-4-1 plasmid and 10 ug of calf thymus carrier DNA. Transfections of the HeLa/C63/tat (clone 9) cells used 0.5 to 10 ug of test plasmid and 10 ug of calf thymus carrier DNA. The HeLa/C63/tat (clone 9) cells were prepared by infection of HeLa cells with helper-free amphotrophic C63-4-1 MoMuLV-tat virus. Following selection in 2mg/ml G418 individual clones were expanded and the expression of tat protein confirmed by immunoprecipitation with monoclonal antibodies to tat (6). Cell extracts were prepared at 48h post-transfection in 150 ul lysis buffer (0.2% NP40, 20 mM Tris pH 8.0, 4 mM $MgCl_2$), heat inactivated at 65° C. for 10 min and stored at −20° C. To ensure that CAT activity was measured in the linear range of the assay (30), at less than 50% conversion of chloramphenicol in its acetylated forms, for each transfection, three different aliquots containing from 5 to 70 ul extract were assayed for CAT activity. Reactions contained extract diluted with lysis buffer to a final volume of 70 ul, 10 ul AcCoA (2.5mg/ml in lysis buffer); 0.5 ul (14C)—chloramphenicol (60 mCi/m mol) and were incubated for 45 min at 37° C. Reaction products were extracted with ethylacetate, separated by thin layer chromatography on silica plates and bands were counted in scintillation fluid to calculate the chloramphenicol conversion efficiency per 10 ul of extract.

Viral LTRs carrying the HIV-1 TAR [SEQ ID NO: 1] region showed increases over basal levels of CAT activity of between 40- and 150 fold in the presence of optimal levels of tat plasmid (FIGS. 8a–d). Mutations in either the bulge region (delta U [SEQ ID NO: 8], U to G [SEQ ID NO: 9], SAS [SEQ ID NO: 5], AAS ) or the loop region (SSA [SEQ ID NO: 3], ASA) produced 4- to 20-fold reductions in trans-activation. Although all LTRs with alterations in the bulge or loop regions were markedly less active than LTRs with intact TAR regions, only the mutant SAA, with alterations to both the upper stem and the loop regions, failed to show a substantial increase in LTR activity over the basal levels at high tat plasmid concentrations. The point mutation G28 to C28 [SEQ ID NO: 10] also produced a defective phenotype, which was restored to wild-type levels by the compensatory mutation C37 to G37 [SEQ ID NO: 11] (FIG. 8a).

In the HeLa/C63/tat cells, the maximal CAT expression promoted by the HIV-1 LTR was 2- to 3-fold lower than CAT expression at optimal tat plasmid concentrations in HeLa cells. This suggests that the levels of tat expression in the HeLa/C63/,tat cells were somewhat lower than the maximum levels of tat expression achieved in the transfected HeLa cells (FIGS. 8e–h). In the HeLa/C63/tat cells, there was no significant increase over basal levels of CAT expression observed for the mutants SSA [SEQ ID NO: 3], SAA, ASA, SAS [SEQ ID NO: 5] or AAS (FIGS. 8g–h). Deletion of the U-rich bulge (delta U [SEQ ID NO: 8], FIG. 8f) or the point mutation G28 to C28 [SEQ ID NO: 10] (FIG. 8e) also produced null phenotypes. In contrast, the ASS [SEQ ID NO: 4] plasmid showed wild-type expression levels (FIG. 8g). However, when G residues were substituted for U residues in the bulge (U to G [SEQ ID NO: 9], FIG. 8f) or when U residues were substituted for G residues in the loop (G to U [SEQ ID NO: 7] FIG. 8f), there was significant CAT activity observed at high plasmid concentrations.

Stoichiometry of tat binding to TAR RNA (FIG. 9)

Initial studies at the Laboratory of Molecular Biology in Cambridge demonstrated sequence-specific interactions between tat protein and TAR RNA (6). However, there was a concern that a significant fraction of the tat might not have been properly folded, and that the estimate made of the dissociation constant ($K_d$ less than 30 nm) was rather approximate, because the measurement was made at high molar excess (1,000 to 10,000-fold) of protein.

Improvements in both the preparation of tat protein and the use of high concentrations of RNA in the binding assays (see below under "Method" and ref 94) have now allowed for the demonstration of complex formation using equivalent concentrations of protein and RNA, and 1 for the study in detail of the sequence requirements for tat binding to TAR RNA.

FIG. 9a shows the results of a saturation binding experiment in which a constant concentration of labeled RNA (10 nM) was incubated with increasing concentrations of tat protein, and the fraction of RNA retained on nitrocellulose filters was measured. Binding was measured by a filter-binding assay as described below under "Method", using monomeric tat protein prepared by CNBr cleavage of a human growth hormone-tat fusion protein expressed in *E. coli*. Reactions for saturation binding contained labeled TAR RNA [SEQ ID NO: 1] or antisense TAR RNA [SEQ ID NO: 6] at 10 nm and between 0 to 300 nM purified tat protein.

Antisense TAR RNA was used as a control, since antisense TAR is unable to form stable complexes with tat in gel-retardation assays (Dingwall et al., 1989).

Tat bound to HIV-1 TAR RNA [SEQ ID NO: 1] with an apparent dissociation constant of $K_d$=12 nM, but binding to antisense RNA [SEQ ID NO: 6] was significantly reduced ($K_d$ greater than 140 nM). Indistinguishable results were obtained using HIV-1 TAR sequences that have either the UUU or UCU bulge sequences found in infectious molecular clones (Table 1).

The stoichiometry of the tat/TAR interaction was determined by varying the TAR RNA concentrations over a wide range, while keeping the tat protein concentration constant near the $K_d$. A Scatchard plot of the data is shown in FIG. 9b. For this Scatchard analysis, the tat protein concentration was held constant at 40 nM and the RNA concentration was varied between 7 nM and 320 nM. The total amount of labeled RNA was kept constant in the binding reactions, but the specific activity of the RNA was varied. The ordinate is the stoichiometry, v, the number of moles of RNA-bound per mole of protein. The abcissa is the ratio of v to the free RNA concentration. The intercept gives a value for the stoichiometry, v, of approximately one, while the slope of the line, fitted to the data by the least squares method, indicates a $K_d$ of 11.8 nM, in excellent agreement with the value obtained from the saturation binding experiment. These results demonstrate that tat forms a one-to-one complex with TAR and that essentially all tat monomers in the new preparations are active in RNA binding.

Method a) Preparation of tat protein

Tat protein was prepared either from beta-galactosidase-tat fusion proteins (6) or from human growth-hormone-tat fusion proteins (85) using an improved method. In brief, inclusion body pellets containing the fusion protein were solubilized in 7 M GdHCl, 50 mM Tris-HCl pH 8.0, 2 mM EDTA, 2 mM DTT and the fusion protein was purified to near homogeneity by ion-exchange chromatography on Q-Sepharose and S-Sepharose (Pharmacia) in buffers containing M Urea, 50 mM Tris-HCl pH 8.0, 2 mM EDTA, 2 mM DTT. The cysteine residues were protected by disulphide-exchange with 20 mM 2-hydroxyethyldisulphide (86), and the protein was cleaved by cyanogen bromide (6). The basic tat protein was then separated from the acidic human growth hormone peptides by ion-exchange chromatography on Q-Sepharose and S-Sepharose in 6 M Urea. The protecting groups were then removed from the protein by addition of 10 mM DTT and the protein refolded by stepwise dialysis against 6 m Urea, 5 M Urea, 3 M Urea, 1 M Urea and 0 M Urea in a buffer containing 50 mM Tris-HCl pH 8.0, 100 uM DTT, 10 uM $ZnCl_2$ Tat protein refolded in this manner elutes as a monomer from Superose 12 columns (Pharmacia) and migrates as a single band on polyacrylamide gels. Protein prepared by both methods behaved comparably in binding assays.

b) Preparation of TAR RNA

RNA transcripts were prepared by transcription with either T3 or T7 RNA polymerases of TAR regions residues +1 to +57, cloned between the HindIII and EcoRi sites of the Bluescribe M13+expression vector (Stratagene). RNA transcripts corresponding to HIV-1 TAR [SEQ ID NO: 1], SSA [SEQ ID NO: 3], SAA and SAS [SEQ ID NO: 5] were synthesized from clones linearized with EcoRI, transcribed with T3 RNA polymerase. RNA transcripts corresponding to the antisense HIV-1 TAR [SEQ ID NO: 6], AAS, ASS [SEQ ID NO: 4] and ASA (not shown) sequences were prepared from the same plasmids linearized with HindIII and transcribed using T7 RNA polymerase. All other RNA molecules were synthesized using T3 RNA polymerase following EcoRI cleavage of the plasmid vector. The RNA products each carry 13 nucleotides of vector sequence at their 5' end and four nucleotides at their 3' ends. Transcription mixtures contained 1 ug linearized plasmid, 40 mM Tris-HCl pH 8.0, 10 MM $MgCl_2$, 2 mM Spermidine-HCl, 50 mM NaCl, 100 uM each ribonucleotide triphosphate, 40 uCi (alpha-$^{32}$ P) UTP (410 Ci/m mol) and 10 units of RNA polymerase in a final volume of 30 ul and were incubated at 37° C. for 30 minutes. After phenol extraction and precipitation from ethanol the RNA was purified from a 9% polyacrylamide denaturing gel. The specific activity of the RNA product was determined and appropriate amounts were used in binding assays.

Large quantities of RNA for competition assays were produced by transcription of 100 ug of the appropriate linear DNA template in a 2.5 ml reaction mixture containing 40 mM Tris-HCl pH 7.6, 25 mM NaCl, 16 mM MgCl$_2$, 10 mM DTT, 3'mM each ribonucleotide triphosphate and 100 ug pure T3 RNA polymerase. The polymerase enzyme was produced by over-expression in *E. coli* BL21 using the plasmid pCM 56 (Morris et al., 1986). The RNA was purified by preparative denaturing gel electrophoresis and 0.5–1 mg pure RNA was routinely produced by this method.

Nuclease digestion experiments (data not shown) have shown that the presence of short extensions on the 3' and 5' sides of TAR RNA do not affect the ability of these sequences to form RNA hairpin loops of the type described by Muesing et al (5). TAR RNA prepared from either the T7 or T3 transcription reactions, or TAR RNA prepared from oligonucleotide templates (6) bind tat indistinguishably. Furthermore, longer RNA molecules which extend the TAR sequence through the first 110 nucleotides of HIV transcripts bind tat equivalently to the 59 nucleotide long transcripts used in most of the experiments conducted (data not shown).

c) Filter binding assays

A wide variety of parameters affecting the binding of tat protein to TAR RNA were studied and binding conditions were optimized. Binding of tat to TAR has a distinct pH optimum at pH 8.0, but good binding is observed between pH 7.5 and pH 8.5. Tat/TAR complexes are very sensitive to ionic strength. Complex formation is strongly inhibited by greater than 100 mM NaCl or 100 mM KCl, the optimum +2 overall ionic strength being 0.08 u+. Addition of $Zn^{+2}$, $Cd^{+2}$, $Ca^{+2}$, $Mg^{+2}$, $Fe^{+2}$ or $Fe^{+3}$ ions to the reaction mixtures does not affect complex formation. However, the binding reaction is sensitive to EDTA at greater than 0.1 mM EDTA. Complex formation is also somewhat temperature sensitive. Optimal binding is observed at 0° C. Between 15° C. and 30° C. there is a 30% reduction in complex formation. See FIG. 2 of reference 110.

For competition experiments, binding reactions (500 ul) were set up on ice and contained 80 pM $^{32}$P-labeled TAR RNA (17,600 dpm, 200 uCi/n mol) and unlabeled TAR RNA to give a final concentration of 20 nM, 0.5 ug calf thymus DNA, 0.2 ug yeast TRNA, 40 units RNAsin (Promega), 50 mM Tris-HCl pH 7.9 and 20 mM KCl. After addition of 0 to 6 uM competitor RNA, binding was initiated by addition of HIV-1 tat protein to a final concentration of 400 ng/mi (40 nM). The binding reaction mixtures were then filtered under reduced pressure through pre-washed nitrocellulose filters (Millipore 0.45 u pore size) and filters were dried and counted by liquid scintillation counting.

Reduced binding of mutant TAR RNAs by tat protein (10, 11, 12, 13, 14, 15, 16, 17)

The graphs shown in FIGS. 10 to 17 illustrate competition for tat binding between TAR RNA and various mutant TAR RNA sequences. Numerical data are given in Tables 2 and 3. In FIGS. 10 and 11 the region unpaired residues at positions 23, 24, 25, 23 being U, is shown to be essential for tat FIGS. 12, 13, 14, 15, 16 and 17 the base stem immediately adjacent to the U-rich bulge be required for efficient tat binding, with there being a requirement for a binding pair at residues 22 and 40 on one side of the bulge, and the base pair G26–C$_{39}$ on the other side of the bulge.

In Tables 2 and 3, $D_{1/2}$ values for various mutant TAR RNA-L sequences are given along with the results of trans-activation experiments in which the altered TAR RNA sequences were introduced into the CAT reporter plasmid D5-3-3. TAR RNA sequences which bind poorly are poor competitors and show increased values for $D_{1/2}$. In every case the mutants that bind tat poorly do not trans-activate efficiently.

Method

Competitor RNA was produced by transcription as described in the method -' or FIG. 7. Binding reactions (500 ul) contained 20 nM TAR RNA, 20,000 dpm $^{32}$P-labeled TAR RNA, 0.5 ug calf thymus DNA, 0.2 ug yeast tRNA, 40 Units RNAsin (Promega), 50 mM Tris-HCl pH 7.5, 1–20 mM KCl in a final volume of 500 ul. After addition of cold competitor RNA in various concentration from 0 to 1000 nM, binding was initiated by addition of 2 ul tat protein (220 ug/ml). The binding reaction mixtures were then filtered through pre-washed nitrocellulose filters (Millipore 0.45 u pore size) and the radioactivity retained on the filters assayed by liquid scintillation counting of the dried filters.

The Binding of Chemically Synthesized RNA by Tat Protein (FIGS. 18 and 19)

FIG. 18 a shows the structure of the full length TAR RNA [SEQ ID NO: 1] of 59 residues that we have shown above is bound by tat protein. Boxed residues are those which appear to be particularly important in specific recognition. The 59-mer is prepared by transcription as described above (FIG. 6). In order to determine whether shorter RNA fragments could be bound by tat protein, a synthetic oligoribonucleotide of 29 residues (FIG. 18*b*) was chemically synthesized of sequence r(GCCAGAUUUGAGCCUGGGAGCUCUCUGGC) [SEQ ID NO: 12] (29-mer) which can fold to generate the top part of TAR including loop and U-rich bulge. This oligonucleotide was prepared by standard solid-phase synthesis methods as described previously (102) using commercially available materials and reagents. Two other oligoribonucleotides were also chemically synthesized using standard methods (102). These are the 17-mer r(AGCCAGAUUUGAGCAGC) [SEQ ID NO: 13, nucleotides 1–17] and the 14-mer r(GCUGCUCUCUGGCU) [SEQ ID NO: 14, nucleotides 2–15]. When annealed, these oligoribonucleotides can form a duplex RNA (FIG. 18*c*) containing the U-rich bulge and flanking base pairs that correspond to the known recognition sequence for tat protein but which lacks the apical loop (103).

FIG. 19 and Table 4 show the results of a competition filter binding assay to compare the binding to tat of 59-mer [SEQ ID NO: 1] transcript with that of chemically synthesized 29-mer [SEQ ID NO: 12] and that of chemically synthesized duplex 14-mer [SEQ ID NO: 14, nucleotides 2–15]+17-mer [SEQ ID NO: 13, nucleotides 1–17]. In these experiments, uniformly $^{32}$-P-labeled transcript (10 nM) was competed against 0–300 nM unlabeled competitor RNA. The results show that both chemically synthesized species (29-mer and 14-mer+17-mer) satisfactorily competed with 59-mer for binding to tat but with 2–3 fold increase in $D_{1/2}$ giving a $K_{rel}$ in each case of 0.4. This demonstrates that chemically synthesized RNA can bind to tat protein and act as an inhibitor of the protein.

Method a) Preparation of 59-mer transcript

This was carried out essentially by the method of Milligan et al. (104). Transcription reactions (0.12 ml for radiolabeled, 0.9 ml for unlabeled) included 0.5 mMa annealed synthetic oligodeoxyribonucleotide template and T7 primer, 40 MM Tris. HCl (pH 8.2 at 37° C.), 10 mM $MgCl_2$, 5 mM DTT, 1 mM spermidine, 0.01% Triton X100, 50 ug/ml acetylated BSA (Anglian Biotech), 0.6% polyethylene glycol 6000 (Koch Light), 2 mM each of ATP, GTP, CTP, and UTP, 3.3 units/ml RNAsin (Promega) and T7 RNA polymerase (10–30 units/ul). For radiolabeling, 100 uCi of alpha-$^{32}$P-UTP was added. The reaction was allowed to proceed for hours at 37° C., stopped by addition of EDTA to 25 mM, phenol extracted and the aqueous phase taken to a pellet by butanol extraction (105) and the desired 59-mer purified by polyacrylamide gel electrophoresis on a 10% gel followed by elution from the gel with 0.5 M ammonium acetate, 1 mM EDTA, 0.5% sodium dodecyl sulphate, and butanol extraction as before (105). The (transcript was stored in 1 mM EDTA (pH 7.4).

b) Chemical Synthesis of Oligoribonucleotides

This was carried out essentially as described previously (102) using an Applied Biosystems 380B DNA Synthesizer and reagents and ribonucleoside phosphoramidites (U, bzA, bzC and ibG) were obtained from Milligan. After deprotection, the oligoribonucleotides were purified by ion exchange h.p.l.c. as described (102) or by polyacrylamide gel electrophoresis as described (102) and stored in sterile water.

c) Competition Binding Assay

Competition binding reactions (0.5 ml) in TK buffer (50 mM Tris.HCl (pH 7.9 at 0.5M and 22° G), 20 mM KCl) included 10 nM $^{32}$P labeled 59-mer (ca. 20,000 cpm), 40nM tat protein, 5 ug/ml calf thymus DNA, 2 ug/ml yeast tRNA, 40 units of RNAsin (Promega) and varying concentrations (0–300 nM) of unlabeled competitor RNA (59-mer [SEQ ID NO: 1;], 29-mer [SEQ ID NO: 12] or preannealed (slow cooled from 90° C.) 14-mer [SEQ ID NO: 14; nucleotides 2–15] and 17-mer [SEQ ID NO: 13; nucleotides 1–17]). Binding was allowed to take place for 2–15 minutes on ice and each reaction was filtered through a twice prewashed (0.6 ml of ice-cold TK buffer) Millipore GS filter (2.5 cm disks, 0.22 um pore) and the filter washed with TK buffer (0.6 ml). Dried filters were counted by liquid scintillation. Results were plotted on a graph (FIG. 19) showing counts retained on the filter versus the concentration of competitor RNA added.

Synthetic TAR analogues where single nucleoside residues are replaced with modified nucleosides (FIGS. 20, 21, 22, 23 and 24).

In order to further define the functional groups on TAR which are involved directly in recognition by tat and also to determine whether modified TAR structures are capable of binding tat protein, TAR analogues were chemically synthesized and compared in their tat-binding properties to unmodified TAR RNA [SEQ ID NO: 1].

Figure 20A:
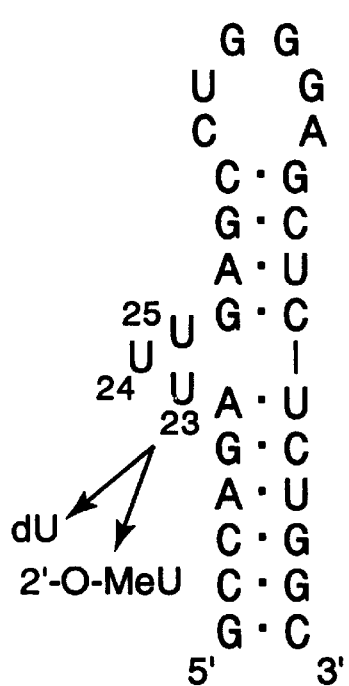
Figure 20B:
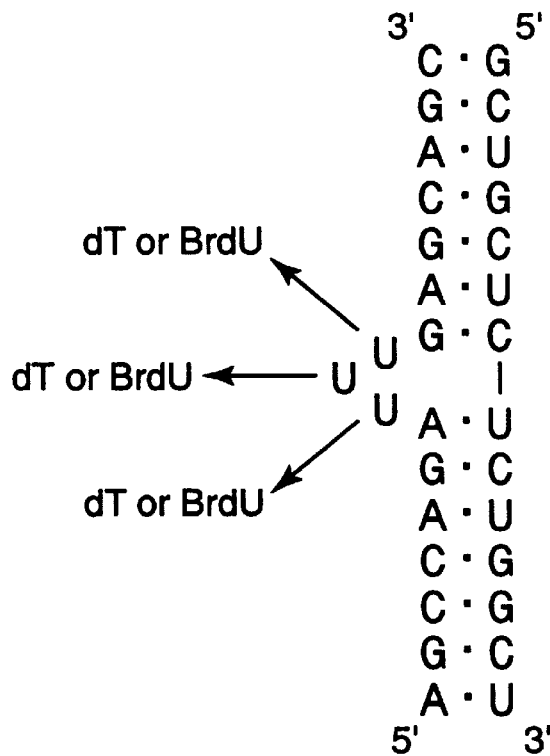

FIG. 20a shows the structures of chemically synthesized 29-mers where the residue corresponding to $U_{23}$ in the TAR sequence has been replaced by either 2'-deoxyuridine (dU) [SEQ ID NO: 15] or by 2'-O-methyluridine (2'-OMeU) [SEQ ID NO: 16]. FIG. 20b shows the structures of RNA duplexes formed from a chemically synthesized 14-mer oligoribonucleotide and a chemically synthesized 17-mer oligoribonucleotide where the residues corresponding to either $U_{23}$, $U_{24}$, or $U_2$, are singly replace by either 2'-deoxythymidine [SEQ ID NO: 17–19, respectively] or by 5-bromo-2'deoxyuridine [SEQ ID NO: 20–22, respectively].

FIG. 21 and Table 4 show the results of a competition filter binding assay to compare the binding to tat of synthetic 29-mer with that of chemically synthesized 29-mers modified at $U_{23}$. In these experiments, $^{32}$P-end-labelled 29-mer (10 nM) was competed against O-120 nM unlabeled competitor RNA. The results show that both chemically synthesized 29-mers containing either dU [SEQ ID NO: 15] or 2'OMeU [SEQ ID NO: 16] competed as well as unmodified 29-mer for binding to tat. This demonstrates that chemically synthesized oligoribonucleotides carrying modifications at sugar residues can bind to tat protein and act as inhibitors of tat protein. Also it is clear that the 2'-hydroxyl group at $U_{23}$ is not likely to be involved in recognition by tat.

FIG. 22 and Table 4 show the results of a competition filter binding assay to compare the binding to tat of synthetic duplex of 17-mer [SEQ ID NO: 13; nucleotides 1–17]+14-mer [SEQ ID NO: 14; nucleotides 2–15] with that of synthetic duplex of 17-mer +14-mer [SEQ ID NO: 14; nucleotides 2–15] where $U_{23}$ [SEQ ID NO: 17] or $U_{24}$ [SEQ ID NO: 18] or $U_{25}$ [SEQ ID NO: 19] has been replaced by 2-deoxythymidine. In these experiments, $^{32}$P-end-labeled 17-mer (10 nm) annealed to unlabeled 14-mer was competed against 0–120 nM unlabeled competitor RNA formed from a modified 17-mer and unmodified 14-mer.

FIGS. 23 and 24 and Table 4 show the results of competition filter binding assays to compare the binding to tat of synthetic duplex of 17-mer [SEQ ID NO: 13; nucleotides 1–17]+14-mer [SEQ ID NO: 14; nucleotides 2–15] with that of synthetic duplex of modified 17-mer +14-mer [SEQ ID NO: 14; nucleotides 2–15] where $U_{23}$ [SEQ ID NO: 20] or $U_{24}$ [SEQ ID NO: 21] or $U_{25}$ [SEQ ID NO: 22] has been replaced by 5-bromo-2'-deoxyuridine. In these experiments, $^{32}$P-end-labelled 29-mer [SEQ ID NO: 12] (10 nM) was competed against 0–120 nM unlabelled competitor RNA formed from a modified 17-mer and unmodified 14-mer.

The results show that substitution by 2'-deoxythymidine at position 23 or 24 had no effect on competition but substitution at position 25 caused a 2–3 fold drop in $D_{1/2}$—Also substitution by 5-bromo-2'-deoxyuridine at positions 24 or 25 has no effect on competition but substitution at position 23 caused a 2-fold drop in $D_{1/2}$. This demonstrates that chemically synthesized oligoribonucleotides containing simultaneously modified sugar and base residues can bind tat protein and act as inhibitors of tat protein.

Method a) $^{32}$P End labeling of 29-mer or 17-mer 50 ul labeling reactions contained ca. 200–300 pmoles 29-mer or 17-mer, 500 pmoles ATP and 40 uC gamma-$^{32}$P-ATP, 50 nM Tris. HCl (pH 7.4), 10 mM $MgCl_2$, 10 mM DTT, 0.77% spermidine and 5 units T4 polynucleotide kinase (NEB) and were carried out at 37° C. for 20–30 minutes. After heating at 90° C. for 2 minutes, a second reaction was carried out with a further 5 units of T4 polynucleotide kinase at 37° C. for 20–30 minutes. The labeled 29-mer or 17-mer was purified by polyacrylamide gel eletrophoresis on a 15% gel (29-mer) or a 20% gel (17-mer), eluted and butanol extracted as described above for the 59-mer transcript and stored in 1 mM EDTA.

b) Synthesis of Modified 29-mers

Chemical synthesis of each modified 29-mer was carried out as described above for unmodified 29-mer except that at the appropriate position a phosphoramidite of 2'deoxyuridine (Glen Research) or of 2'-O-methyluridine (Glen Research) was added in the coupling reaction. Purification was by polyacrylamide gel electrophoresis as described previously (102).

c) Synthesis of Modified 17-mers

Chemical synthesis of 17-mers carrying -5-bromo-2'-deoxyuridine modifications were carried out as described above for unmodified 17-mer except that at the appropriate position a phosphoramidite of 5-bromo-2'-deoxyuridine (Glen Research) was added in the coupling reaction. Chemical synthesis of 17-mers carrying 2'-deoxythymidine modifications were carried out by the methods described previously (102) but with the ribophosphoramidites of guanosine and adenosine protected by phenoxyacetyl (obtained from ABN) and at the appropriate position thymidine phosphoramidite (Applied Biosystems) was added in the coupling reaction. Ammonia deprotection of these oligonucleotides was carried out under modified conditions (saturated methanolic ammonia at room temperature for 20–24 hours). All modified 17-mers were purified by ion exchange h.p.l.c. as previously described (102).

c) Competition Binding Assays

Competition binding reactions (0.5 ml) in TK buffer included 10 nM duplex formed from $^{32}$P-labeled and unlabeled 29-mer (ca. 20,000 cpm) or 10 nM duplex formed from $^{32}$P-labeled and unlabeled 17-mer annealed to unlabeled 14-mer, 40 nM tat protein, 5 ug/ml calf thymus DNA, 2 ug/ml yeast tRNA and varying concentrations (0–120 nM) of unlabeled competitor RNA (29-mer or modified 29-mer (FIG. 21), or 17-mer +14-mer duplex or modified 17-mer +14-mer duplex (22, 23 and 24) and were carried out as described above.

Enhanced binding of chemically synthesized modified TAR to tat protein

FIG. 25 shows the structures of RNA duplex formed from a chemically synthesized 15-mer oligoribonucleotide [SEQ ID NO: 14] and a chemically synthesized 18-mer oligoribonucleotide where the residues corresponding to either $U_{23}$ [SEQ ID NO: 23]$_1$, $U_{24}$ [SEQ ID NO: 24] or $U_{25}$ [SEQ ID NO: 25] are singly replaced by 4-thio-2'-deoxythymidine.

FIG. 26 and Table 4 show the results of a competition filter binding assay to compare the binding tat of synthetic duplex of 18-mer [SEQ ID NO: 13]+15-mer [SEQ ID NO: 14] with that of synthetic duplex of modified 18-mer +15-mer [SEQ ID NO: 14] where $U_{23}$ [SEQ ID NO: 23] or $U_{24}$ [SEQ ID NO: 24] or $U_{25}$ [SEQ ID NO: 25] has been replaced by 4-thio-2'-deoxythymidine. In these experiments, $^{32}$P-end labelled 18-mer (10 nM) annealed to unlabelled 15-mer was competed against 0–120 nM unlabelled competitor RNA (duplex formed from unmodified 18-mer [SEQ ID NO: 13] and 15-mer [SEQ ID NO: 14], duplex formed from a modified 18-mer and unmodified 14-mer [SEQ ID NO: 14; nucleotides 2–15], or 59-mer [SEQ ID NO: 1]). In the same experiment, 15-mer [SEQ ID NO: 14] and 18-mer [SEQ ID NO: 13] duplex competed as well as 17-mer [SEQ ID NO: 13; nucleotides 1–17] and 14-mer [SEQ ID NO: 14; nucleotides 2–15] (not shown). The results show that in each case the duplex containing 4-thio-2'-deoxythymidine [SEQ ID NO: 23–25] substitution competed better than the unmodified 15-mer +18-mer duplex. This demonstrates that chemically modified oligoribonucleotides can bind to tat better than unmodified oligoribonucleotides and thus can act as better inhibitors of tat protein.

Method a) Synthesis of oligoribonucleotides containing 4-thio-2'-deoxythymidine 18-mer oligoribonucleotides containing 4-thio-2'deoxythymidine were synthesized as previously described (102) except that the ribophosphoramidites were as follows: adenosine and cytidine were protected by tbutylphenoxyacetyl (gift from Dr N. Sinha, Milligen), guanosine by phenoxyacetyl (ABN) and the 4-thio amidite 0 as 5'-O-dimethoxytrityl S-(p-nitrophenyl)-4-thiothymidine 2-cyanoethyl-N, N-diisopropylphosophoroamidite (106, 107) (gift from Dr B. Connolly, University of Soijthampton). This amidite (10 mg in anhydrous acetonitrile, 0.75 ml) was used at the appropriate point in the assembly cycle. Removal of p-nitrophenyl groups and base protecting groups at the end of the synthesis was carried out as described (107) except that ammonia deprotection was with ammonium hydroxide/ethanol (3:1) at room temperature for 16–24 hours. oligonucleotides were purified by ion exchange h.p.l.c. as described previously and stored in sterile water. Analysis of the oligonucleotides by digestion with snake venom phosphodiesterase and alkaline phosphatase showed that no 5-methyl-2'-deoxycytidine had been formed during the ammonia deprotection of the 4-thio T derivative.

b) Synthesis of unmodified 18-mer [SEQ ID NO: 13] and 15-mer [SEQ ID NO: 14]

These were chemically synthesized as previously described above (102).

c) Competition Binding Assays

Competition binding reactions (0–5 ml) in TK buffer included 10 nM duplex formed from $^{32}$P-labelled (ca. 20,000 cpm) and unlabelled 18-mer [SEQ ID NO: 13] annealed to unlabelled 15-mer [SEQ ID NO: 14], 40 nM tat protein, 5 ug/ml calf thymus DNA, 2 ug/ml yeast TRNA and varying concentrations (0–120 nM) of unlabelled competitor RNA (59-mer [SEQ ID NO: 1] or 18-mer [SEQ ID NO: 13]+15-mer [SEQ ID NO: 14] duplex, or modified 18-mer [SEQ ID NO: 23–25]+15-mer [SEQ ID NO: 14] duplex, or modified 18-mer duplexes) and were carried out as described.

Discussion

The sequence-specific recognition of TAR exhibited by tat explains the requirement for tat in HIV trans-activation. TAR RNAs derived from the first stem loop of the HIV-2 LTR can bind HIV-1 tat and are trans-activated by HIV-1 tat (8, 9, 20, 25). TAR RNA mutations which alter the U-rich bubble sequence, or disrupt the TAR stem loop structure, abolish tat binding and also fail to trans-activate.

Tat recognition of TAR requires the presence of protruding U-residues in the context of a double-helical segment and the $G_{26}$–$C_{39}$ base pair. As long as Watson-Crick base pairing is maintained, the identity of other base pairs throughout the TAR stem make relatively minor contributions to the RNA structure required for transactivation (10, 12, 27) or tat binding (6, 94). Binding of proteins to sequences including bulged residues in RNA stem-loops is not without precedent. R17 coat protein binding is critically dependent upon the presence of a bulged A residue (32) in the R17 packaging sequence. The dissociation constant of tat for TAR (12 nM) is typical for a RNA binding protein. For example, a $K_d$ of 3 nM has d been measured for both the Rev-RRE complex (33, 34) and factor binding to the iron-response element RNA stem-loop (35).

Furthermore, the bulge region need not contain only uridine residues in order to bind tat or to trans-activate the viral LTR. HIV-1 TAR [SEQ ID NO: 1] sequences with either UCU or UUU bulge sequences found in infectious HIV-1 clones, can bind tat with equivalent affinities and both of these sequences are efficiently trans-activated. In vivo data suggests that in the context of a bulge, only the residue $U_{23}$ is essential for tat recognition of TAR (11). Mutation of $U_{23}$ to A has been reported to reduce trans-activation to 18% of wild-type levels, but the mutations $U_{24}$ to A and $U_{25}$ to G only reduce trans-activation by 42% and 49%, respectively (11).

Furthermore, as shown here, mutation of $U_{24}$ to C or $U_{25}$ to C has only minor effect on trans activation and tat binding, whereas mutation of $U_{23}$ to C dramatically reduces tat binding to TAR RNA and trans activation. Although this suggests that tat recognizes $U_{23}$ the conformation of TAR may also be important. In RNA stem loop structures, bulged residues introduce bends or kinks which vary depending on the number and types of bases in the bulge and their positions in the stem (87). The first stem-loop of HIV-2 TAR [SEQ ID NO: 2] has a bulge which contains a base equivalent to $U_{23}$ but because in this sequence the bulge contains only two uridine residues, its affinity for EIV-1 tat is reduced 2.5-fold.

Sequences in the TAR RNA loop, which are not required for tat binding, are nonetheless important for transactivation. TAR sequences with substitution of residues in either the bulge or loop domains show reduced, but measurable, trans-activation. It seems likely that host RNA-binding proteins participate in trans-activation by binding to the loop sequences (36, 37). The partial activation of some of the TAR substitution mutations, observed at high plasmid levels, indicates that a poor binding site on TAR, for either tat or the host proteins, could allow for limited factor binding. Double mutations in which both the U-rich bulge and the loop are altered IR show substantially lower levels of trans-activation than do the equivalent mutations in a single region.

Kao et al. (38) and Selby et al. (12) have proposed that tat acts indirectly as an anti-terminator and helps to overcome a block to elongation at or near the TAR site. Their model is based on observations that short prematurely terminated RNA transcripts accumulate in the absence of tat (12, 38, 39). Additional support for the model comes from nuclear run-on experiments which suggest that HIV-1 transcription initiation complexes are stabilised in the presence of tat (40) and evidence that TAR is functional on nascent chains (16). However, anti-termination is unlikely to occur at TAR itself, since mutations in TAR which abolish trans-activation, or deletions of TAR, do not result in constitutively high levels of LTR expression (5, 12, 19, 27, 28) and it is difficult to "chase" the short RNA transcripts into fulllength mRNAs in the presence of tat (40). A modified version of the Kao and Selby model, in which the TAR site functions as a loading site for RNA polymerase co-factors, in a manner analogous to the bacteriophage nut site (12), therefore seems to be more appropriate. In transcription through the nut region produces RNA binding sites for the N protein, as well as the host proteins nusa and nusb, and allows asembly of a transcription complex composed of RNA polymerase and these co-factors (41, 42) which is able, to overcome activity at distal terminators (43). It is suggested that in the tat/TAR system, tat and host co-factors assemble with RNA polymerase in a reaction mediated by the protein binding sites present on nascenttranscripts. A modified polymerase could then stimulate viral mRNA production by overcoming blocks to elongation at a variety of distal sites.

It will be clear from the above that because tat has a high affinity for a specific binding U. site on TAR, it is likely that compounds capable of interfering in vitro with tat binding to TAR will prove to be effective anti-HIV agents.

Subsequent to the initial filing of this patent there have been two reports which show that the over-expression of TAR RNA in vivo from synthetic genes can result in the inhibition of HIV growth or gene activation (108, 109). Over-expression of the TAR RNA sequence acts as a decoy, or competitor inhibitor, and prevents the binding of tat protein to the HIV-encoded TAR RNA sequence. As a result there is no activation of viral gene expression and no generation of progeny virus.

TABLE 1

Binding of HIV-1 tat to HIV-1 Tar [SEQ ID NO: 1] and mutant TAR sequences

|  | $K_d$ | $D_{1/2}$ | $K_{Rel}$ |
|---|---|---|---|
| HIV-1 TAR (UUU) | 12 nM | 64 nM | 1.00 |
| HIV-1 TAR (UCU) | 12 nM |  |  |
| HIV-2 TAR [SEQ ID NO: 2] | 30 nM | 160 nM | 0.40 |
| $G_{28}$ to $C_{28}$ [SEQ ID NO: 10] | >100 nM | 680 nM | 0.09 |
| $G_{28}$ to $C_{28}$; $C_{37}$ to $G_{37}$ [SEQ ID NO: 11] | 24 nM | 76 nM | 0.84 |
| delta U (bulge) [SEQ ID NO: 8] | >70 nM | 420 nM | 0.15 |
| G to U (loop) [SEQ ID NO: 7] | 25 nM | 66 nM | 0.97 |
| U to G (bulge) [SEQ ID NO: 9] | >100 nM | 420 nM | 0.15 |
| Antisense [SEQ ID NO: 6] | >140 nM | — | — |

The dissociation constant for HIV-1 TAR [SEQ ID NO: I] was calculated from the Scatchard plot shown in FIG. 9. Dissociation constants ($K_d$) for the TAR mutants were estimated by the half-maximal binding observed in filter binding assays and these are somewhat less reliable than for HIV-1 TAR since less data were used in the determination and saturation conditions were not always obtained. A better measure of tat affinity for the mutant sequences is $D_{1/2}$, the concentration of competitor RNA that reduces the binding of HIV-1 tat to HIV-1 TAR RNA to 50%. $K_{Rel}$ is the ratio of the $D_{1/2}$ values for HIV-1 TAR and competitor RNA.

TABLE 2

Effect of Nucleotide Substitutions on tat binding to TAR RNA [SEQ ID NO: 1] and on transactivation in vivo
1. Mutations in the U-rich bulge

| Mutation | $D_{1/2}$ (nM) | Units CAT activity/ 500 ng plasmid |
|---|---|---|
| Wild types: UUU, UCU | 90 | 14,400 |
| UUC | 800 | 10,800 |
| UUC | 100 | 8,400 |
| UU | 100 | 4,200 |
| U | 673 | 1,420 |
| CUU | 630 | 1,250 |
| CCU | 1,330 | 1,850 |
| CCC | 1,778 | 840 |
| CUC | 2,137 | 430 |
| CC | 2,372 | 1,100 |

TABLE 3

Effect of Nucleotide Substitutions on tat binding to TAR RNA [SEQ ID NO: 1] and transactivation in vivo
II. Mutations in the stem surrounding the U-rich bulge

| activity Mutations (nM) | $D_{1/2}$ (nM) | Units CAT 500 ng plasmid |
|---|---|---|
| wild-type | 90 | 5,600 |
| A22 to G22 | 63 | 5,000 |
| U40 to A40 | 5,623 | 760 |
| A22 to U22; U40 to A40 | 220 | 4,150 |
| C39 to G39 | 1,496 | 80 |
| G26 to C26; C39 to G39 | 2,371 | 13 |
| G26 to A26; C39 to U39 | 631 | 290 |

TABLE 4

| Duplex | D½ (nM) | K$_{rel}$ (59-mer [SEQ ID NO: 1]) | K$_{rel}$ (29 [SEQ ID NO: 12] or 14 [SEQ ID NO: 14; nucleotides 2–15] + 17 [SEQ ID NO: 13; nucleotides 1–17]) |
|---|---|---|---|
| <u>59-mer</u> [SEQ ID NO: 1] | 40 | 1.0 | |
| 29-mer [SEQ ID NO: 12] | 100 | 0.4 | |
| 14 [SEQ ID NO: 14; nucleotides 2–15] + 17 [SEQ ID NO: 13, nucleotides 1–17] | 110 | 0.4 | |
| <u>29-mer</u> [SEQ ID NO: 12] | 60 | | 1.0 |
| dU-23 [SEQ ID NO: 15] | 55 | | 1.1 |
| 2'-OmeU-23 [SEQ ID NO: 16] | 50 | | 1.2 |
| 14 [SEQ ID NO: 14; nucleotides 2–15] + <u>17</u> [SEQ ID NO: 13; nucleotides 1–17] | 40 | | 1.0 |
| dT-23 [SEQ ID NO: 17] | 35 | | 1.1 |
| dT-24 [SEQ ID NO: 18] | 30 | | 1.2 |
| dT-25 [SEQ ID NO: 19] | 90 | | 0.4 |
| BrdU-23 [SEQ ID NO: 20] | 70 | | 0.6 |
| BrdU-24 [SEQ ID NO: 21] | 45 | | 1.0 |
| BrdU-25 [SEQ ID NO: 22] | 35 | | 1.1 |
| 15 [SEQ ID NO: 14] + <u>18</u> [SEQ ID NO: 13] | 65 | 0.3 | 0.8 |
| 14 [SEQ ID NO: 14; nucleotides 2–15] + 17 [SEQ ID NO: 13; nucleotides 1–17] | 50 | 0.4 | 1.0 |
| 59-mer [SEQ ID NO: 1] | 18 | 1.0 | 2.8 |
| 4-thioT-23 [SEQ ID NO: 23] | 32 | 0.6 | 1.6 |
| 4-thioT-24 [SEQ ID NO: 24] | 25 | 0.7 | 2.0 |
| 4-thioT-25 [SEQ ID NO: 25] | 12 | 1.5 | 4.2 |

Table 4:
D½ (concentration of competitor RNA required to reduce by half the binding of $^{32}$P RNA to filter in presence of tat) and K$_{rel}$ (relative values of D$_{1/2}$) for various chemically synthesized RNA compared to transcript 59-mer [SEQ ID NO: 1] or chemically synthesised 29-mer [SEQ ID NO: 12] or 14 [SEQ ID NO: 14; nucleotides 2-15] + 17 [SEQ ID NO: 13; nucleotides 1–17] duplex.
All values of D½ are estimated from competition curves and are subject to deviation by 20%.
Underlining indicates the identity of the $^{32}$P RNA.

REFERENCES

1. Dayton, A. I., Sodroski, J. G., Rosen, C. A., Goh, W. C. & Haseltine, W. A. Cell 44, 941–947 (1986). (The trans-activator gene of human T cell lymphotropic virus type III is required for replication).
2. Rosen, C. A., Sodroski, J. G., Goh, W. C., Dayton, A. I., Loppke, J., & Haseltine, W. A. Nature 319, 555–559 (1986).
3. Fisher, A. G., Feinberg, M. B., Josephs, S. F., Harper, M. E., Marselle, L. M., Reyes, G., Gonda, M. A., Aldovini, A., Debouck, C., Gallo, R. C., & Wong-Staal, F. Nature 320, 367–371 (1986). (The trans-activator gene of HTLV-III is essential for virus replication).
4. Hauber, J., Perkins, A., Heimer, E. P., & Cullen, B. R. Proc. Natl. Acad. Sci. USA 84, 6364–6368 (1987).
5. Muesing, M. A., Smith, D. H. & Capon, D. J. Cell 48, 691701 (1987). (Regulation of mRNA accumulation by a human immunodeficiency virus trans-activator protein).
6. Dingwall, & C., Emberg, I., Gait, M. J., Green, S. M., Heaphy, S., Kam, J., Lowe, A. D., Singh, M., Skinner, M. A., & Valerio, R. Proc. Natl. Acad. Sci. U.S.A. 86, 6925–6929 (1989). (Human immunodeficiency virus I tat protein binds trans-activation-responsive region (TAR) RNA in vitro).
7. Muller, W. E. G., Okamoto, T., Reuter P., Ugarkovic, D., & Schroder, H. C. J. Biol. Chem. 265, 3803–3808 (1990).
8. Guyader, M., Emerman, M., Sonigo, P., Clavel, F., Montagnier, L. & Alizon, M. Nature 326, 662–66.9 (1987). (Genome organization and trans-activation of the human immunodeficiency virus type 2).
9. Emerman, M., Guyader, DI., Montagnier, L., Baltimore, D. & Muesing, M. A. EMBO J. 6, 3755–3760 (1987). (The specificity of the human immunodeficiency virus type 2 transactivator is different from that of human immunodeficiency virus type 1).
10. Roy, S., Parkin, N. T., Rosen, C. A., Itovitch, J. & Sonenberg, N. J Virol. 64, 1402–1406 (1990). (Structural requirements for trans activation of human immunodeficiency virus type 1 long terminal repeatdirected gene expression by tat: Importance of basepairing, loop sequences and bulges in the tat-responsive sequence).
11. Berkhout, B. & Jeang, K-T. J. Virol. 63, 5501–5504 (1989). (Trans activation of human immunodeficiency virus type 1 is sequence specific for both the single-stranded bulge and loop.of the trans-acting responsive hairpin: A quantitative analysis).
12. Selby, M. J., Bain, E. S., Luciw, P. & Peterlin, B. M. Genes Dev.3, 547–558 (1989). (Structure, sequence and position of the stem-loop in tar determine transcriptional elongation by tat through the HIV-1 long terminal repeat).
13. Hauber, J. & Cullen, B. R. J. Virol. 62, 673–679 (1988). (Mutational analysis of the trans-activation responsive region of human immunodeficiency virus type I long terminal repeat).
14. Jakobovits, A., Smith, D. H., Jakobovits, E. B. & Capon, D. J. Mol. Cell Biol. 8, 2555–2561 (1988). (A discrete element 3' of human immunodeficiency virus I (HIV-1) and HIV-2 mRNA initiation sites mediates transcriptional activation by an HIV trans activator).
15. Peterlin, B. M., Luciw, P. A., Barr, P.3., & Walker, M. D. Proc. Natl. Acad. Sci. U.S.A. 83, 9734–9738 (1986).
16. Berkhout, B., Silverman, R. H. & Jeang, K.- T. Cell 59, 273–282 (1989). (Tat trans-activates the human immunodeficiency virus through a nascent RNA target).
17. Sharp, P. A. & Marciniak, R. A. Cell 59, 229–230 (1989).
18. Jakobovits, A., Rosenthal, A. & Capon, D. J. EMBO J. 9, 1165–1170 (1990).
19. Cullen, B. R. Cell 46, 973–982 (1986).
20. Berkhout, B., Gatignol, A., Silver, J., & Jeang, K.- T. Nucl. Acids. Res. 18, 1839–1846 (1990).
21. Parkin, N. T., Cohen, E. A., Darveau, A., Rosen, C., Haseltine, W., & Sonnenberg, N. EMBO 3. 7, 2831–2837 (1988).
22. Edery, I., Petryshyn, R., & Sonnenberg, N. Cell 56, 303–312 (1988).
23. Rice, A. P., & Matthews, M. B. Nature 332, 551–553 (1988).
24. Braddock, M., Chambers, A., Wilson, W., Esnouf, M. P., Adams, S. E., Kingsman, A. J., & Kingsman, S. M. Cell 5 8, 269–279 (1989).
25. Fenrick, R., Malim, M. H., Hauber, J., Lee, S.- Y., Maizel, J. & Cullen, B. R. J. Virol. 63, 5006–5012 (1989).
26. Morris, C. E., Klement, J. F. & McAllister W. T. Gene 41, 192–200 (1986).
27. Feng, S. & Holland, E. C. Nature 334, 165–168 (1988). (Hiv-1 tat trans-activation requires the loop sequence within TAR).
28. Garcia, J. A., Harrich, D., Soultanakis, E., Wu, F., Mitsuyasu, R. & Gaynor, R. B. EMBO J. 8, 765–778 (1989). (Human immunodeficiency virus type 1 LTR TATA and TAR region sequences required for transcriptional regulation).
29. Adachi, A., Gendelman, H. E., Koenig, S., Folks, T., Willey, R., Rabson, A. & Martin, M. E. J. Virol. 59, 284291 (1986).
30. Gorman, C. M., Padmanabliam, R. & Howard, B. H. Science 222, 551–553 (1983).
31. Gorman, C. M., Moffat, L. F. & Howard B. H. Mol. Cell Biol. 2, 1044–1051 (1982).
32. Wu, H.- N. & Uhlenbeck, O. C. Biochemistry, 26, 8221–8227 (1987).
33. Heaphy, S., Dingwall, C., Emberg, I., Gait, M. J., Green, S. M., Karn, J., Lowe, A. D., Singh, M. and Skinner, M. Cell, 60, 685–693 (1990). (HIV-1 regulator of virion expression (rev) protein binds to an RNA stem-loop structure located within the rev-response element region).
34. Daly, T. J., Cook, K. S., Gary, G. S., Maione, T. E. & Rusche, J. R. Nature, 342, 816–819 (1989). (Specific binding of HIV-1 recombinant rev protein to the revresponsive element in vitro).
35. Leibold, E. A., Laundano, A., & Yu, Y. Nucl. Acids Res. 18. 1819–1825 (1990).
36. Gaynor, R., Soultanakis, E., Kuwabara, M., Garcia, J., & Sigman, D. S. Proc. Natl. Acad. Sci. U.S.A. 86, 4858–4862 (1989).
37. Gatignol. A., Kumar, A., Rabson, A., & Jaeng K.- T. Proc. Natl. Acad. Sci. U.S.A. 86, 7828–7832 (1989).
38. Kao, S.- Y., Calman, A. F., Luciw, P. A. & Peterlin, B. M. Nature 330, 489–493 (1987). (Anti-termination of transcription within the long terminal repeat of HIV-1 by tat gene product).
39. Toohey, M. G. & Jones, K. A. Genes Dev. 3, 265–283 (1989).
40. Laspia, M. F., Rice, A. P. & Matthews, M. B. Cell 59, 283–292 (1989). (HIV-1 tat protein increases transcriptional initiation and stabilizes elongation).
41. Barik, S., Ghosh, B., Whalen, W., Lazinski, D., & Das, A. Cell 50, 885–899. (1987).
42. Lazinski, D., Grzadzielska, E. & Das, A. Cell 59, 207–218 (1989).
43. Gottesman, M. E., Adhya, S., & Das, A. J. Mol. Biol. 140, 57–75 (1980).
44. Agrawal, S., Goodchild, J., Civiera, M. P., Thornton, A. H., Sarin, P. S. and Zamecnik, P. C. (1988), Proc. Natl. Acad. Sci. U.S.A. 85, 7079–7083.
45. Brill, W. K.-D., Tang, J- Y., Ma, Y- X. and Caruthers, M. H. (1989), J. Amer. Chem. Soc., 111,2321–2322.
46. Chang, D. A. and Sharp, P. A. (1989) Cell 59, 789–795). (Regulation by HIV rev depends upon recognition of splice site).
47. Cohrane, A. W., Chen, C.- H. and Rosen, C. A. (1990) Proc. Natl. Acad. Sci (USA) 87, 1198–1202. (Specific interaction ot the human immunodeficiency virus rev protein with a structured region in the env mRNA).
48. Connolly, B. A., and Newman, P. C., (1989) Nucleic Acids Res., 17,4957–4974.
49. Cosstick, R. and Vyle, J. S. (1989) Tetrahedron Letters, 30, 4693–4696.
50. Cullen, B. R., Huber, J., Campbell, K., Sodroski, J. G., Haseltine, W. A. and Rosen C. A. (1988) J. Virol. 62, 2498–2501. (Subcellular location of the human immunodeficiency virus trans-acting art gene-product).
51. Dayton, E. T., Powell, D. M. and Dayton, A. I. (1989) Science 246, 1625–1629. (Functional analysis of CAR, the target sequence for the rev protein of HIV-1).
52. Emerman, M., Vazeaux, R. and Peden, K. (1989) Cell 57, 1155–1165. (The rev gene product of the human immunodeficiency virus affects envelope specific RNA localization).
53. Feinberg, M. B., Jarrett, R. F., Aldovini, A., Gallo, R. C. and Wong-Stall, F. (1986). Cell 46, 807–817. (HTLV-III expression and production involve complex regulation at the levels of splicing and translation of viral RNA).
54. Felber, B. K., Hadzopoulou-Cladaras, M., Cladaras, C., Copeland, T. and Pavlakis, G. N. (1989). Proc. Natl. Acad. Sci. (USA) 86, 1495–1499). (Rev protein of human immunodeficiency virus type 1 affects the stability and transport of the viral mRNA).
55. Gait, M. J., Jones, A. S. and Walker, R. T. (1974) J. Chem. Soc. Perkin I, 1684–1686.
56. Gait, M. J., Jones, A. S., Jones, M. D., Shepherd, M. J. and Walker, R. T. (1979) J. Chem. Soc. Perkin 1, 1389–1394.
57. Helene, C., Montenay-Garestier, T., Saison, T., Takasugi, M., Toulme, J. J., Asseline, U., Lancelot, G., Maurizot, J. C., Toulme, F. and Thuong, N. T. (1985) Biochimie, 67, 777–783.
58. Jones, A. S., (1979) Int. J. Biolog. Mac-romolecules,1, 194–207.
59. Kim, S., Bym, R., Groopman, J. and Baltimore, D. (1989) J. Virol. 63, 3708–3713. (Temporal aspects of DNA and RNA synthesis during human immunodeficiency virus infection: Evidence for differential gene expression).
60. Knight, D. M., Flomerfelt, F. A. and Ghrayeb, J. (1987) Science 236, 837–840 (Expression of the art/trs protein of HIV and study of its role in viral envelope synthesis).
61. Krug, A., Oretyskaya, T. S., Volkov, E. M., Cech, D., Shabarova, Z. A. and Rosenthal, A. (1989) Nucleosides and Nucleotides, 8, 1473–1483.

62. Lemaitre, M., Bayard, B. and Lebleu, B. (1987) Proc. Natl. Acad. Sci, USA, 84, 648–652.
63. Letsinger, R. L., Zhang, G., Sun, D. K., Ikeuchi, T. and Sarin, P. (1989) Proc. Natl. Acad. Sci. USA, 86, 6553–6556.
64. Mag, M. and Engels, J. W. (1988) Nucleic Acids Res., 16, 3525–3543.
65. Malim, M. H., Hauber, J., Le, S.- Y., Maizel, J. V. and Cullen, B. R. (1989a) Nature (London) 338, 254–257. (The HIV-1 rev trans-activator acts through a structured target sequence to activate nuclear export of unspliced viral mRNA).
66. Malim, M. H., Bohnlein, S., Fenrick, R., Le, S.- Y. Maizel, J. V. and Cullen, B. R. (1989b) Proc. Natl. Acad. Sci. (USA) 86, 8222–8226. (Functional comparison of the rev trans-activators encoded by different primate immunodeficiency virus species).
67. Malim, M. H., Bohnlein, S., Hauber, J. and Cullen, B. R. (1989c) Cell 58, 205–214. (Functional dissection of the HIV-1 rev trans-activator: Derivation of a transdominant repressor of rev function).
68. Malim, M. H., Tiley, L. S., McCarn, D. F., Rusche, J. R., Hauber, J. and Cullen, B. R. (1990) Cell 60, 675–683. (HIV-1 structural gene expression requires binding of the rev trans-activator to its RNA target sequence).
69. Miller, P. S., Dreon, N., Pulford, S. M. and McParland, K. B. (1980) J. Biol. Chem., 255, 9569–9665.
70. Miller, P. S., Chandrasegaran, S., Dow, D. L., Pulford, S. M. and Kim, L. S. (1982) Biochemistry, 21, 5468–5474.
71. Miller, P. S., Blake, K. R., Cushman, C. D. Kean, J. M., Lee, B. L., Lin, S-B, and Murakamni, A. (1988) Nucleic Acids Res. Special Pub. No. 20, 113–114.
72. Morvan, F., Rayner, B., Inbach, J. L., Thenet. S., Bertrand, J. R., Paoletti, J., Malvy, C. and Paoletti, C. (1987) Nucleic Acids Res., 15, 3421–3437.
73. Olsen, H. S., Nelbrock, P., Cohrane, A. W., Rosen, C. A. (1990) Science 247, 845–848. (Secondary structure is the major determinant for interaction of HIV-rev protein with RNA)
74. Perrouault, L., Asseline, U., Rivalle, C., Thuong, N. T., Bisagni, E., Giovannangeli, C., Le Doan, T. and Helene, C. (1990) Nature, 344, 358–360.
75. Piccirilli, J. A., Krauch, T., Moroney, S. E. and Benner, S. A. (1990) Nature, 343, 33–37.
76. Rimsky, L., Hauber, J., Dukovich, M., Malim, M. H., Langlois, A., Cullen, B. R. and Greene, W. C. (1988) Nature (London) 335, 738–740. (Functional replacement of the HIV-1 rev protein by the HTLV-1 rex protein).
77. Rosen, C. R., Terwilliger, E., Dayton, A. I., Sodrowski, J. G. and Haseltine, W. A. (1988) Proc. Natl. Acad. Sci. (USA) 85, 2071–2075. (Intragenic cis-acting responsive sequences of the human immunodeficiency virus).
78. Sadaie, M. R., Benter, T. and Wong-Staal, F. (1988) Science 239, 910–913. (Site directed mutagenesis of two trans-regulatory genes (tat-III, trs) of HIV-1).
79. Sodrowski, J., Goh, W. C., Rosen, C. A., Dayton, A., Terwilliger, E. and Haseltine, W. A. 2 (1986) Nature (London) 321, 412–417. (A second post-transcriptional activator gene required for HTLV-III replication).
80. Sproat, B. S., Lamond, A. I., Beijer, B., Neuner, P. and Ryder, U. (1989) Nucleic Acids Res., 17, 3373–3386.
81. 81. Stein, C. A., Subasinghe, C., Shinozuka, K, and Cohen, J. S. (1988) Nucleic Acids Res., 15, 3209–3221.
82. Sun, J- S., Francois, J-C., Lavery, R., Saison-Behmoaras, T., Montenay-Garestier, T. Thuong, N. T. and Helene, C. (1988) Biochemistry, 27, 6039–6045.
83. Vlassov, V. V., Gaidamakov, S. A., Zarytova, V. F., Knorre, D. G., Levina, A. S., Nikonova, A. A. Podust, L. M. and Fedorova, O. S. (1988) Gene, 72, 313–322.
84. Zapp, M. L. and Green, M. R. (1989) Nature (London) 342, 714–716. (Sequence-specific binding by the HIV-1 rev protein).
85. Ikehara, M., Ohtsuka, E., Tokunga, T., Taniyama, Y., Iwai, S., Kitano, K., Miyamoto, T., Ohgi T., Sakuragawa, Y., Fujiyama, K., Ikari, T., Kobayashi, M., Miyake, T., Shibahara, S., Ono, S., Ueda, T., Tanaka, T., Baba, H., Miki, T., Sakurai, A., Oishi, T., Chisaka, O. & Matsubara, K. (1984) Proc. Natl. Acad. Sci. USA, 81, 5956–5960.
86. Smithies, O. (1965) Science, 150, 1595–1598.
87. Bhattacharyya, A., Murchie, A. I. H. & Lilley, D, M, (1990) Nature, 343, 484–487.
88. Selby M J, Bain E S, Luciw P, Peterlin B M. Structure, sequence and position of the stem-loop in TAR determine transcriptional elongation by tat through the HIV-1 long terminal repeat. Genes & Dev. 1989, 3:547–558.
89. Laspia M F, Rice A P, Mathews M B. Synergy between HIV-1 tat and adenvovirus Ela is principally due to stabilization of transcriptional elongation. Genes & Development 1990 4:2397–2408.
90. Braddock M, Thorburn A M, Chamber A, Elliott G D, Anderson G J, Kingsman A J, Kingsman, S M. A nuclear translation block imposed by the HIV-1 U3 region is relieved by the tat-TAR interaction. Cell 1990, 62:1123–1133.
91. Chin D J, Selby M J, Peterlin B M. Human immunodeficiency virus type 1 tat does not trans-activate mature trans-acting responsive region RNA species in the nucleus or cytoplasm or primate cells. J. Virol. 1991, 65:1758–1764.
92. Roy S, Agy M, Hovanessian A G, Sonenberg N, Katze M G. The integrity of the stem structure of human immunodeficiency virus type 1 tat-responsive structure RNA is required for interaction with the interferon-induced 68,000-M4 protein kinase. 1991, 65:632–640
93. Gunnery S, Rice A P, Robertson H D, Mathews M B. HIV-1 TAR RNA can prevent activation of the protein kinase DAI. Proc. Natl. Acad. Sci. USA 1990, 87:8686–8691.
94. Dingwall C, Emberg I, Gait M J, Green S M, Heaphy S, Karn J, Lowe AD, Singh M, Skinner M A. HIV-1 tat protein stimulates transcription by binding to a U-rich bulge in the stem of the TAR RNA structure. EMBO J. 1990, 9:4145–4153.
95. Cordingley M G, LaFemina R L, Callahan P L, Condra J H, Sardana V V, Graham D J, Nguyen T M, LeGrowk K, Gotlib L, Schlabach A J, Colonno R J. Sequence specific interaction of tat and tat peptides with the TAR sequence of HIV-1 in vitro. Proc. Natl. Acad. Sci. USA 1990, 87:8985–8989.
96. Weeks, K M, Ampe C, Schultz S C, Steitz T A, Crothers D M. Fragments of the HIV-1 tat protein specifically bind TAR RNA. Science 1990, 249:1281–1285.
97. Southgate C, Zapp M L, Green M R. Activation of transcription by HIV-1 tat protein tethered to nascent 84. Zapp, M. L. and Green, M. R. (1989) Nature (London) 342, 714–716. (Sequence-specific binding by the HIV-1 rev protein). RNA through another protein. Nature 1990, 345:640–642.
98. Selby M J, Peterlin B M. Trans-activation by HIV-1 tat via a heterologous RNA binding protein. Cell. 1990, 62:769–776.
99. Berkhout B, Gatignol A, Rabson A B, Jeang K-T. TAR independent activation of the HIV-1 LTR: Evidence that tat requires specific region of the promoter. Cell 1990, 62: 757–767.
100. Okamoto T, Benter T, Josephs S G, Sadaie J R, Wong-Staal F. Transcriptional activation from the long-term repeat of the human immunodeficiency virus in vitro. Virology 1990, 63:606–614.
101. Marciniak R A, Calnan B J, Frankel A D, Sharp P A. HIV-1 tat protein trans-activates transcription in vitro. Cell. 1990, 63:791–802.
102. Gait, M J, Pritchard, C and Slim, G. (1991) in "Oligonucleotides and their Analogues: A Practical Approach", F. Eckstein (ed.), Oxford University Press, 2548.
103. Sumner-Smith, M., Roy, S., Barnett, R. W., Kuperman. R., Reid, L. S. and Sonenberg. N. (1991) Abstracts of IUB Conference on Nucleic Acids Therapeutics, Jan. 13–17, 1991, Clearwater Beach, Fla., p94.
104. Milligan, J. F., Groebe, D. R., Witherell, G. W. and Uhlenbeck, O. C. (1987) Nucleic Acids Res., 15, 8784–8799.
105. Cathala, G. and Brunel, C. (1990) Nucleic Acids Res., 18, 201.
106. Nikoforov, T. T., Connolly, B. A. (1991) Tetrahedron Letts., 32, 2505–2508.
107. Nikiforov, T. T., Connolly, B. A. (1991) Tetrahedron Letts., in press.
108. Sullenger, B. A., Gallardo, H. F., Ungers, G. E. and Gilboa, E. (1990) Cell 63, 601–608.
109. Graham, G. J., Maio, J. J. (1990) Proc. Natl. Acad. Sci. USA 87, 5817–5821.
110. Dingwall, C., Emberg, I., Gait, M. J., Heapy, S., Karn, J., and Skinner, M. Trans-activation requires the binding of the HIV-1 tat protein to TAR RNA, Advances for AIDS, 1991, 133–143.

What is claimed is:

1. An RNA oligonucleotide consisting of the nucleotide sequence:

r(GCCAGAUUUGAGCCUGGGAGCUCUCUGGC) (SEQ ID NO: 12)

r(GCCAGA-dU-UUGAGCCUGGGAGCUCUCUGGC) (SEQ ID NO: 13)

or

R(GCCAGA-2'-OmeU-UUGAGCCUGGGAGCUCUCUGGC). (SEQ ID NO: 16)

2. An assay for identifying a compound that inhibits binding of tat protein to TAR RNA, comprising incubating tat protein with an oligonucleotide that binds to HIV tat protein, wherein said oligonucleotide comprises two or three unpaired nucleotides flanked at both the 3' and 5' sides by at least one nucleotide which forms a flanking base pair with another nucleotide in said oligonucleotide, wherein the unpaired nucleotides contain a uridine nucleotide corresponding to $U_{23}$ found in the sequence of HIV TAR RNA (SEQ ID NO: 1), and wherein one of the flanking base pairs is a G:C base pair corresponding to $G_{26}$:$C_{39}$ in the sequence of HIV TAR RNA (SEQ ID NO: 1), in the presence of a test inhibitor compound, and determining the amount of tat protein which is bound to said oligonucleotide, wherein decreased binding of tat protein to said oligonucleotide in the presence of the test inhibitor compound relative to binding in the absence of said test inhibitor compound is indicative of inhibition.

3. An assay for identifying a compound that inhibits binding of tat protein to TAR RNA, comprising incubating tat protein with an oligonucleotide of claim 12 in the presence of a test inhibitor compound, and determining the amount of tat protein which is bound to said oligonucleotide, wherein decreased binding of tat protein to said oligonucleotide in the presence of the test inhibitor compound relative to binding in the absence of said test inhibitor compound is indicative of inhibition.

\* \* \* \* \*

UNITED STATES PATENT AND TRADEMARK OFFICE
CERTIFICATE OF CORRECTION

PATENT NO. : 6,114,109

DATED : September 5, 2000

INVENTOR(S) : Jonathan Karn

It is certified that error appears in the above-identified patent and that said Letters Patent is hereby corrected as shown below:

Column 44, line 27, after "claim" delete "12" and insert ----- 1 -----.

Signed and Sealed this

Twenty-ninth Day of May, 2001

Attest:

NICHOLAS P. GODICI

Attesting Officer　　　　Acting Director of the United States Patent and Trademark Office

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 59 bases
      (B) TYPE: nucleic acid
      (C) STRANDEDNESS: single
      (D) TOPOLOGY: linear (ii) MOLECULE TYPE: mRNA (xi) SEQUENCE DESCRIPTION: SEQ ID NO: 1:

GGGUCUCUCU GGUUAGACCA GAUUUGAGCC UGGGAGCUCU CUGGCUAACU AGGGAACCC      59

(2) INFORMATION FOR SEQ ID NO: 2:

(i) SEQUENCE CHARACTERISTICS:
      (A) LENGTH: 53 bases
      (B) TYPE: nucleic acid
      (C) STRANDEDNESS: single
      (D) TOPOLOGY: linear (ii) MOLECULE TYPE: mRNA (xi) SEQUENCE DESCRIPTION: SEQ ID NO: 2:

CUGCGGAGAG GCUGGCAGAU UGAGCCCUGG GAGGUUCUCU CCAGCACUAG CAG      53

(2) INFORMATION FOR SEQ ID NO: 3:

(i) SEQUENCE CHARACTERISTICS:
      (A) LENGTH: 59 bases
      (B) TYPE: nucleic acid
      (C) STRANDEDNESS: single
      (D) TOPOLOGY: linear (ii) MOLECULE TYPE: mRNA (xi) SEQUENCE DESCRIPTION: SEQ ID NO: 3:

GGGUCUCUCU GGUUAGACCA GAUUUGAGCU CCCAGGCUCU CUGGCUAACU AGGGAACCC      59

(2) INFORMATION FOR SEQ ID NO: 4:

(i) SEQUENCE CHARACTERISTICS:
      (A) LENGTH: 59 bases
      (B) TYPE: nucleic acid (C) STRANDEDNESS: single
            (D) TOPOLOGY: linear (ii) MOLECULE TYPE: mRNA (xi) SEQUENCE DESCRIPTION: SEQ ID NO: 4:

GGGUUCCCUA GUUAGACCAG AUUUGAGCCU GGGAGCUCUC UGGCUAACCA GAGAGACCC        59

(2) INFORMATION FOR SEQ ID NO: 5:

(i) SEQUENCE CHARACTERISTICS:
            (A) LENGTH: 59 bases
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO: 5:

GGGUCUCUCU GGUUAGCCAG AGAGCCUGGG AGCUCAAAUC UGGUCUAACU AGGGAACCC        59

(2) INFORMATION FOR SEQ ID NO: 6:

(i) SEQUENCE CHARACTERISTICS:
            (A) LENGTH: 59 bases
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO: 6:

GGGUUCCCUA GUUAGCCAGA GAGCUCCCAG GCUCAAAUCU GGUCUAACCA GAGAGACCC        59

(2) INFORMATION FOR SEQ ID NO: 7:

(i) SEQUENCE CHARACTERISTICS:
            (A) LENGTH: 59 bases
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO: 7:

GGGUCUCUCU GGUUAGACCA GAUUUGAGCC UUUUAGCUCU CUGGCUAACU AGGGAACCC        59

(2) INFORMATION FOR SEQ ID NO: 8:

(i) SEQUENCE CHARACTERISTICS:
            (A) LENGTH: 56 bases
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO: 8:

GGGUCUCUCU GGUUAGACCA GAGAGCCUGG GAGCUCUCUG GCUAACUAGG GAACCC          56

(2) INFORMATION FOR SEQ ID NO: 9:

(i) SEQUENCE CHARACTERISTICS:
            (A) LENGTH: 59 bases
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO: 9:

GGGUCUCUCU GGUUAGACCA GAGGGGAGCU CCCAGGCUCU CUGGCUAACU AGGGAACCC          59

(2) INFORMATION FOR SEQ ID NO: 10:

(i) SEQUENCE CHARACTERISTICS:
        (A) LENGTH: 59 bases
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO: 10:

GGGUCUCUCU GGUUAGACCA GAUUUGACCC UGGGAGCUCU CUGGCUAACU AGGGAACCC          59

(2) INFORMATION FOR SEQ ID NO: 11:

(i) SEQUENCE CHARACTERISTICS:
        (A) LENGTH: 59 bases
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO: 11:

GGGUCUCUCU GGUUAGACCA GAUUUGACCC UGGGAGGUCU CUGGCUAACU AGGGAACCC          59

(2) INFORMATION FOR SEQ ID NO: 12:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: synthetic RNA (xi) SEQUENCE DESCRIPTION: SEQ ID NO: 12:

GCCAGAUUUG AGCCUGGGAG CUCUCUGGC          29

(2) INFORMATION FOR SEQ ID NO: 13:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: synthetic RNA (xi) SEQUENCE DESCRIPTION: SEQ ID NO: 13:

AGCCAGAUUU GAGCAGCU          18

(2) INFORMATION FOR SEQ ID NO: 14:

(i) SEQUENCE CHARACTERISTICS:
        (A) LENGTH: 15 bases
        (B) TYPE: nucleic acid
        (C) STRANDEDNESS: single
        (D) TOPOLOGY: linear (ii) MOLECULE TYPE: synthetic RNA (xi) SEQUENCE DESCRIPTION: SEQ ID NO: 14:

AGCUGCUCUC UGGCU          15

(2) INFORMATION FOR SEQ ID NO: 15:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: synthetic RNA (ix) FEATURE:
        (A) NAME/KEY: misc_feature
        (B) LOCATION: 7
        (D) OTHER INFORMATION: N is 2'-deoxyuridine (xi) SEQUENCE DESCRIPTION: SEQ ID NO: 15:

GCCAGANUUG AGCCUGGGAG CUCUCUGGC                                                29

(2) INFORMATION FOR SEQ ID NO: 16:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: synthetic RNA (ix) FEATURE:
        (A) NAME/KEY: misc_feature
        (B) LOCATION: 7
        (D) OTHER INFORMATION: N is 2'-O-methyluridine (um)

(xi) SEQUENCE DESCRIPTION: SEQ ID NO: 16:

GCCAGANUUG AGCCUGGGAG CUCUCUGGC                                                29

(2) INFORMATION FOR SEQ ID NO: 17:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: synthetic RNA (ix) FEATURE:
        (A) NAME/KEY: misc_feature
        (B) LOCATION: 8
        (D) OTHER INFORMATION: N is 2'-deoxythymidine (xi) SEQUENCE DESCRIPTION: SEQ ID NO: 17:

AGCCAGANUU GAGCAGC                                                                  17

(2) INFORMATION FOR SEQ ID NO: 18:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: synthetic RNA (ix) FEATURE:
        (A) NAME/KEY: misc_feature
        (B) LOCATION: 9
        (D) OTHER INFORMATION: N is 2'-deoxythymidine (xi) SEQUENCE DESCRIPTION: SEQ ID NO: 18:

AGCCAGAUNU GAGCAGC                                                    17

(2) INFORMATION FOR SEQ ID NO: 19:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: synthetic RNA (ix) FEATURE:
        (A) NAME/KEY: misc_feature
        (B) LOCATION: 10
        (D) OTHER INFORMATION: N is 2'-deoxythymidine (xi) SEQUENCE DESCRIPTION: SEQ ID NO: 19:

AGCCAGAUUN GAGCAGC                                                    17

(2) INFORMATION FOR SEQ ID NO: 20:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: synthetic RNA (ix) FEATURE:
        (A) NAME/KEY: misc_feature
        (B) LOCATION: 8
        (D) OTHER INFORMATION: N is 5-bromo-2'-deoxyuridine (xi) SEQUENCE DESCRIPTION: SEQ ID NO: 20:

AGCCAGANUU GAGCAGC                                                    17

(2) INFORMATION FOR SEQ ID NO: 21:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: synthetic RNA (ix) FEATURE:
        (A) NAME/KEY: misc_feature
        (B) LOCATION: 9
        (D) OTHER INFORMATION: N is 5-bromo-2'-deoxyuridine (xi) SEQUENCE DESCRIPTION: SEQ ID NO: 21:

AGCCAGAUNU GAGCAGC                                                    17

(2) INFORMATION FOR SEQ ID NO: 22:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: synthetic RNA (ix) FEATURE:
        (A) NAME/KEY: misc_feature
        (B) LOCATION: 10
        (D) OTHER INFORMATION: N is 5-bromo-2'-deoxyuridine (xi) SEQUENCE DESCRIPTION: SEQ ID NO: 22:

AGCCAGAUUN GAGCAGC                    17

(2) INFORMATION FOR SEQ ID NO: 23:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: synthetic RNA (ix) FEATURE:
        (A) NAME/KEY: misc_feature
        (B) LOCATION: 8
        (D) OTHER INFORMATION: N is 4-thio-2'-deoxythymidine (xi) SEQUENCE DESCRIPTION: SEQ ID NO: 23:

AGCCAGANUU GAGCAGCU                   18

(2) INFORMATION FOR SEQ ID NO: 24:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: synthetic RNA (ix) FEATURE:
        (A) NAME/KEY: misc_feature
        (B) LOCATION: 9
        (D) OTHER INFORMATION: N is 4-thio-2'-deoxythymidine (xi) SEQUENCE DESCRIPTION: SEQ ID NO: 24:

AGCCAGAUNU GAGCAGCU                   18

(2) INFORMATION FOR SEQ ID NO: 25:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: synthetic RNA (ix) FEATURE:
        (A) NAME/KEY: misc_feature
        (B) LOCATION: 10
        (D) OTHER INFORMATION: N is 4-thio-2'-deoxythymidine (xi) SEQUENCE DESCRIPTION: SEQ ID NO: 25:

AGCCAGAUUN GAGCAGCU                   18

(2) INFORMATION FOR SEQ ID NO: 26:

(i) SEQUENCE CHARACTERISTICS:
        (A) LENGTH: 243
        (B) TYPE: nucleic acid
        (C) STRANDEDNESS: single
        (D) TOPOLOGY: unknown (ii) MOLECULE TYPE: mRNA (ix) FEATURE:
        (A) NAME/KEY: RRE (xi) SEQUENCE DESCRIPTION: SEQ ID NO: 26:

-continued

```
CAGUGGGAAU AGGAGCUUUG UUCCUUGGGU UCUUGGGAGC AGCAGGAAGC ACUAUGGGCG        60

CAGCGUCAAU GACGCUGACG GUACAGGCCA GACAAUUAUU GUCUGGUAUA GUGCAGCAGC       120

AGAACAAUUU GCUGAGGGCU AUUGAGGCGC AACAGCAUCU GUUGCAACUC AAGUCUGGGG       180

CAUCAAGCAG CUCCAGGCAA GAAUCCUGGC UGUGGAAAGA UACCUAAAGG AUCAACAGCU       240

CCU                                                                    243
```